US006495332B2

(12) United States Patent
Ulevitch et al.

(10) Patent No.: US 6,495,332 B2
(45) Date of Patent: **\*Dec. 17, 2002**

(54) METHODS AND COMPOSITIONS FOR AMELIORATING THE SYMPTOMS OF SEPSIS

(75) Inventors: Richard Ulevitch, Del Mar, CA (US); Peter Tobias, Encinitas, CA (US); Samuel D. Wright, New York, NY (US); John C. Mathison, San Diego, CA (US)

(73) Assignees: The Sripps Research Institute, La Jolla, CA (US); The Rockefeller University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/970,338

(22) Filed: Oct. 2, 2001

(65) Prior Publication Data

US 2002/0034509 A1 Mar. 21, 2002

Related U.S. Application Data

(63) Continuation of application No. 09/542,118, filed on Apr. 3, 2000, now Pat. No. 6,297,049, which is a division of application No. 08/906,400, filed on Aug. 5, 1997, now Pat. No. 6,045,795, which is a division of application No. 08/328,554, filed on Oct. 25, 1994, now Pat. No. 5,730,980, which is a continuation of application No. 07/990,378, filed on Dec. 15, 1992, now abandoned, which is a continuation of application No. 07/387,817, filed on Aug. 1, 1989, now abandoned.

(51) Int. Cl.[7] ......................... G01N 33/53; C12Q 1/02; C12N 5/06
(52) U.S. Cl. ..................... 435/7.2; 435/29; 435/334
(58) Field of Search ......................... 435/7.2, 29, 334

(56) References Cited

U.S. PATENT DOCUMENTS

| 4,834,976 A | 5/1989 | Rosol et al. ................... 424/87 |
| 4,918,163 A | 4/1990 | Young et al. ................. 530/387 |
| 5,057,598 A | 10/1991 | Pollack et al. .............. 530/387 |
| 5,730,980 A | * 3/1998 | Ulevitch et al. ......... 424/154.1 |

OTHER PUBLICATIONS

Schutt et al., *Immunol. Letters* 19: 32–328, 1988.*
Ashmun, et al., Blood, 69:886–892 (1987).
Bazil, et al., "Eur. J. Immunol.", 16:1583–1589 (1986).
Beutler, et al., "Science", 229:869 (1985).
Beutler, et al., "N. Eng. J. Med.", 316:379 (1987).
Ehlenberger, et al., "J. Exp. Med.", 145:357–371 (1977).
Espevik, et al., "J. Immunol. Meth.", 95:99–105 (1986).
Ferrero, et al., "Nucleic Acids Research", vol. 16:4173 (1988).
Goyert, et al., "Science", 239:497–500 (1988).
Mathison, et al., "J. Clin. Invest.", 81:1925 (1988).
Michie, et al., "New Eng. J. Med.", 318:1481–1486 (1988).
Tobias, et al., "J. Exp. Med.", 164:777–793 (1986).

(List continued on next page.)

*Primary Examiner*—Hankyel T. Park
(74) *Attorney, Agent, or Firm*—Gray Cary Ware & Freidenrich LLP; Lisa A. Haile

(57) ABSTRACT

The present invention concerns a method of treating sepsis comprising administering a therapeutically effective amount of anti-CD14 antibody molecules. A therapeutic composition comprising anti-CD14 antibody molecules in a pharmaceutically acceptable excipient is also contemplated.

6 Claims, 9 Drawing Sheets

OTHER PUBLICATIONS

Tobias, et al., "J. Biol. Chem.", 263:13479–13481 (1988).
Tobias, et al., "J. Biol. Chem.", 264:10867–10871 (1989).
Tracey, et al., "Nature", 330:662–664 (19870.
Van Deventer, et al., "Lancet", 1:605–608 (1988).
Van Voorhis, et al., J. Exp. Med., 158:126–145 (1983).
Waage, et al., "Lancet", 1:355–357 (1987).
Wright, et al., "J. Exp. Med.", 156:1149–1164 (1982).
Wright, et al., "J. Exp. Med.", 158:1338–1343.
Wright, et al., "Proc. Natl. Acad. Sci. USA", 80:5699–5703 (1983).
Wright, et al., "L. Exp. Med.", 164:1876–1888 (1986).
Greishman, et al., Experimental Gram NG. Bacterial Sepsis Prevention of Mortality not preventable by antibiotics alone.
Tracey, et al., "Anti–cacheclin/TNF monoclonal antibodies prevent septic shock during lethal bacteralmia".
Spalding, Bio ?Technology, "In Shockery Synergey Sepsis tallies third victim" 428–429 (Apr. 1993.
Gibbs, Scientific American, "Try, Try Again making antibodies more useful by making them more human" 101–103 (Jul. 1993).
Hinshaw, et al., "Surg. Gynecol and Obstetrics" 145:1–11, 1977.
Hess, et al., "Surg. Gynecol & Obstetrics" 166:147–153 1988.
Cross, et al., "Infection and Immunity" 61:2741–2747 1993.
Fink, et al., "Journal of Surg. Res."49:186–196 1990.
Schuett, et al., "Immunology Lett." 19:321–328, 1988.
Oden, et al., "Develop Biol. Standard" 24:181–187, 1974.
Speigers, et al., "Vaccine" 7:364–368, 1984.
Cross, et al., "The Journal of Endotoxin Research" pp. 57–69, 1994.
Bogman, et al., "Diagnosis of Renal Allograft Rejection by Macrophage Immunostaining with a CD14 Monoclonal Antibody, WT14", The Lancet, 235–238, 1989.

* cited by examiner

METHODS AND COMPOSITIONS FOR AMELIORATING THE SYMPTOMS OF SEPSIS

The present application is a continuation and claims the benefit of priority under 35 USC § 120 of U.S. application Ser. No. 09/542,118, filed Apr. 3, 2000, which issued as U.S. Pat. No. 6,297,049 on Oct. 2, 2001, which is a divisional of U.S. application Ser. No. 08/906,400, filed on Aug. 5, 1997, and issued as U.S. Pat. No. 6,045,795, which is a divisional of U.S. application Ser. No. 08/328,55, filed on Oct. 25, 1994, and issued as U.S. Pat. No. 5,730,980, which is a continuation of U.S. application Ser. No. 07/990,378, filed on Dec. 15, 1992 which is abandoned, which is a continuation of U.S. application Ser. No. 07/387,817, filed on Aug. 1, 1989, which is abandoned. The disclosure of the prior application is considered part of and is incorporated by reference in the disclosure of this application.

DESCRIPTION

1. Technical Field

The present invention relates to methods and compositions for preventing or treating sepsis. More particularly, the present invention relates to molecules that bind the CD14 monocyte differentiation antigen or LPS-LBP complexes, thereby inhibiting the binding of LPS-LBP complexes by CD14-expressing cells.

2. Background

Sepsis is a morbid condition induced by a toxin, the introduction or accumulation of which is most commonly caused by infection or trauma. The initial symptoms of sepsis typically include chills, profuse sweat, irregularly remittent fever, prostration and the like, followed by persistent fever, hypotension leading to shock, neutropenia, leukopenia, disseminated intravascular coagulation, adult respiratory distress syndrome and multiple organ failure.

Sepsis-inducing toxins have been found associated with pathogenic bacteria, viruses, plants and venoms. Among the well described bacterial toxins are the endotoxins or lipopolysaccharides(LPS) of the gram-negative bacteria. These molecules are glycolipids that are ubiquitous in the outer membrane of all gram-negative bacteria. While chemical structure of most of the LPS molecule is complex and diverse, a common feature is the lipid A region of LPS [Rietschel, E. Th. et al., in *Handbook of Endotoxins*, 1:187–214 eds. R. A. Proctor and E. Th. Rietschel, Elsevier, Amsterdam (1984)]; recognition of lipid A in biologic systems initiates many, if not all, of the pathophysiologic changes of sepsis. Because lipid A structure is highly conserved among all types of gram-negative organisms, common pathophysiologic changes characterize gram-negative sepsis.

Current concepts support the contention that the primary response of the host to LPS (including man) involves the recognition of LPS by cells of the monocyte/macrophage lineage, followed by the rapid elaboration of a variety of cell products including the general group known as cytokines. Other cell types believed to participate in sepsis and in particular in the response to LPS are polymorphonuclear leukocytes and endothelial cells; each of these cell types are also capable of responding to LPS with the elaboration of potent inflammatory substances.

LPS is believed to be a primary cause of death in humans during gram-negative sepsis, particularly when the symptoms include adult respiratory distress syndrome (ARDS). van Deventer et al., *Lancet*, 1:605 (1988); Ziegler et al., *J. Infect. Dis.*, 136:19–28 (1987). For instance, one particular cytokine, tumor necrosis factor alpha/cachectin (TNF), has recently been reported to be a primary mediator of septic shock. Beutler et al., *N. Eng. J. Med.*, 316:379 (1987). Intravenous injection of LPS endotoxin from bacteria into experimental animals and man produces a rapid, transient release of TNF. Beutler et. al., *J. Immunol.*, 135:3972(1985). Mathison et al., *J. Clin. Invest.* 81:1925 (1988). Evidence that TNF is a critical mediator of septic shock comes primarily from experiments in which pretreatment of animals with anti-TNF antibodies reduces lethality. Beutler et al., *Science*, 229:869, (1985). Mathison et al., *J. Clin. Invest.* 81: 1925 (1988). These reports suggest that interruption of the secretion of TNF caused by LPS or other factors would ameliorate the often lethal symptoms of sepsis.

[0006] Upon introduction of LPS into the blood, it may bind to a protein termed lipopolysaccharide binding protein (LBP). LBP is a 60 kD glycoprotein present at concentrations of less than 100 ng/ml in the serum of healthy animals and man. During the acute phase, LBP is synthesized by hepatocytes, and reaches concentrations of 30–50 ug/ml in serum. LBP can be purified from acute phase human and rabbit serum. Tobias, et al., *J. Exp. Med.*, 164:777–793 (1986). LBP recognizes the lipid A region of LPS and forms high affinity, 1:1 stoichiometric complexes with both rough and smooth form LPS. Tobias, et al., *J. Biol. Chem.*, 264:10867–10871 (1989). LBP bears N-terminal sequence homology with the LPS-binding protein known as bactericidal permeability-increasing factor, (BPI). Tobias, et al., *J. Biol. Chem.*, 263:13479–13481, (1988) BPI is stored in the specific granules of PMN [Weiss, et al., *Blood*, 69:652–659, (1987)] and kills gram negative bacteria by binding LPS and disrupting the permeability barrier. Weiss, et al., *J. Immunol.*, 132:3109–3115, (1984). In contrast to BPI, LBP is not directly cytotoxic for gram-negative bacteria [Tobias, et al., *J. Biol. Chem.*, 263:13479–13481, (1988)] and its precise biological function has been obscure.

By way of further background, the cells of the monocyte/macrophage lineage perform diverse immune function including the phagocytosis of microorganisms, the uptake of antigenic material and its presentation in a form which is stimulatory to helper T cells. They are probably also involved in the immune surveillance against tumors and they secrete some complement components and cytokines. Surface membrane antigens play a critical role in regulating these activities. Several monocyte/macrophage surface antigens have been identified and their molecular weight has been determined. One such antigen, CD14, is a 55-kD glycoprotein expressed by monocytes, macrophages, and activated granulocytes. It is recognized by a number of monoclonal antibodies (mAbs) including MO2, MY4, 3C10 and LEUM3. Although no biological function has yet been ascribed to CD14, its restricted expression on mature cells suggests an important effector function. The nucleotide sequence of the gene encoding the monocyte cell surface differentiation antigen CD14 has been determined and the amino acid residue sequence of CD14 has been deduced therefrom. (Ferrero et al., *Nucleic Acids Research* Vol. 16:4173 (1988)

BRIEF SUMMARY OF THE INVENTION

The present invention was born out of the discovery that a primary regulator of cytokine production and release is the CD14 receptor, particularly in cells of the monocyte/macrophage lineage. Inasmuch as cytokines secretion plays an important role in producing the symptoms of sepsis, the present invention contemplates methods and agents for inhibiting the secretion of cytokines, particularly TNF.

Therefore, in one embodiment, the present invention contemplates administering, preferably intravenously, to a pateint at risk for or suffering the symptoms of sepsis a therapeutically effective amount of an anti-CD14 antibody, an anti-LBP antibody, an LBP peptide analog or a subcombination or combination thereof. The method can be practiced alone or in combination with the substantially simultaneous administration of other therapeutic modalities known to prevent or ameliorate the symptoms of sepsis, including treatment with one or more of an antiboiotic, steroids, anti-TNF antibody, TNF antagonist and the like.

Further contemplated by the present invention are therapeutic compositions, typically in unit dose form, useful for preventing or ameliorating the symptoms of sepsis. The compositions comprise a pharmaceutically acceptible carrier containing one or more of an anti-CD14 antibody, an anti-LBP antibody, and LBP peptide analog that acts as an LBP antagonist, as an active ingredient. In preferred embodiments, a therapeutic composition of this invention further contains, as active ingredients an agent known to prevent or ameliorate the symptoms of sepsis, such as an antibiotic, steroid, anti-TNF antibody, a TNF antagonist, soluble CD14 and the like, either alone, in sub-combination or combination.

BRIEF DESCRIPTION OF THE DRAWINGS

In the Figures forming a portion of the disclosure of this invention.

DETAILED DESCRIPTION OF THE INVENTION

A. Definitions

Figure 1:
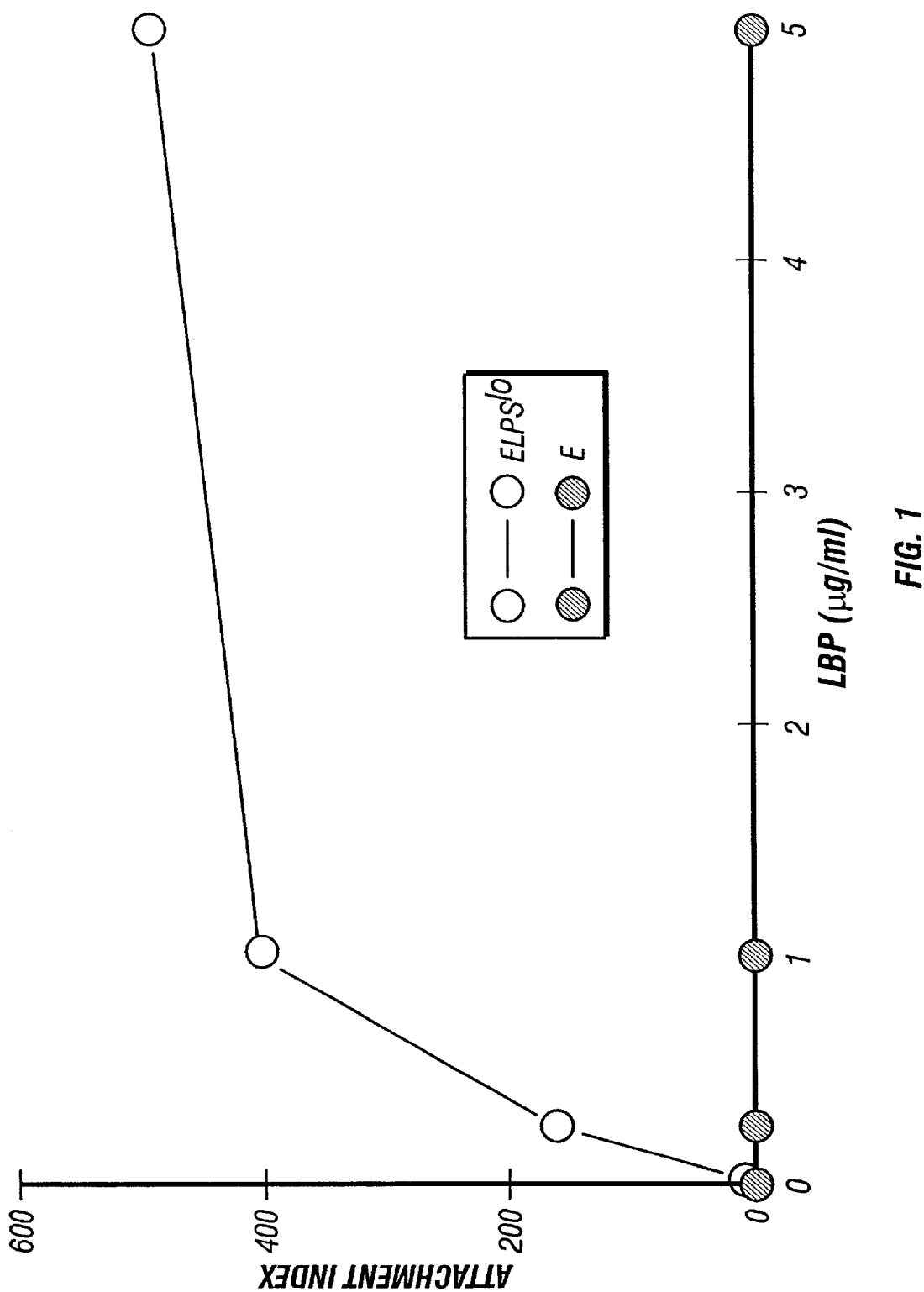
FIG. 1 illustrates that LBP enhances the interaction of ELPS with MO. Monolayers of MO were incubated with E or ELPS$^{lo}$ in the presence of varying doses of LBP, and attachment index was scored. A control acute phase protein, mannose binding protein (MBP) (5 ug/ml) caused no enhancement of binding of ELPS$^{lo}$ (attachment index 4.9). Results are representative of 4 separate experiments.

Amino Acid Residue: The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH2 refers to the free amino group present at the amino terminus of a polypeptide. C00H refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

TABLE OF CORRESPONDENCE

| SYMBOL 1-Letter | AMINO ACID | 3-Letter |
|---|---|---|
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Try | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino acid residues.

The term "antibody" in its various grammatical forms refers to a composition containing immunoglobulin molecules and/or immunologically active portions of immunoglobulin molecules, i.e., molecules that contain an antibody combining site or paratope. In preferred embodiment, the antibodies used herein have been affinity purified.

An "antibody combining site" is that structural portion of an antibody molecule comprised of heavy and light chain variable and hypervariable regions that specifically binds antigen.

The phase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the thereapeutic methods described herein.

Fab and F(ab')$_2$ portions of antibody molecules are prepared by the proteolytic reaction of papin and pepsin, respectively, on substantially intact antibody molecules by methods that are well known. See for example, U.S. Pat. No. 4,342,566 to Theofilopolous et al. (The disclosures of the art cited herein are hereby incorporated by reference.). Fab' antibody molecule portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred, and is utilized as illustrative herein.

The phrase "monoclonal antibody" in its various grammatical forms refers to an antibody containing having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific (chimeric) monoclonal antibody.

The phrase "substantially simultaneously" is used herein to mean within a time period sufficient to produce concurrent results, e.g., bacterial lysis as a result of antibiotic administration and amelioration or prevention of symptoms of sepsis that may occur as a result of that lysis by administration of an anti-CD14 antibody, anti-LBP antibody, LBP peptide analog, or a subcombination or combination thereof, as described herein.

[0027] The phrase "pharmaceutically acceptable" refers to molecular entities and compositions that are physiologically tolerable and do not typically produce an allergic or similar untoward reaction, such as gastric upset, dizziness and the like, when administered to a human.

B. Therapeutic Methods

The present invention contemplates methods of treating and/or preventing one or more of the symptoms of sepsis, particularly those associated with a transient increase in the blood level of TNF, such as fever, hypotension, neutropenia, leukopenia, thrombocytopenia, shock and multiple organ failure. Patients in need of such treatment include those at risk for or suffering toxemia, such as endotoxemia resulting from a gram-negative bacterial infection, serpent venom poisoning, hepatic failure, and the like. In addition, some patients having a gram-positive bacterial, viral or fungal infection display the symptoms of sepsis and may benefit from a therapeutic method of this invention. Patients particularly able to benefit from the present invention are those suffering infection by *E. coli*, *Haemophilus influenza* B, *Neisseria meningitides*, *staphylococci*, or *pneumococci*. Patients at risk for sepsis include those suffering burns, gunshot wounds, renal or hepatic failure due to chemical poisoning or abuse, and the like.

Thus, in one embodiment, the present invention contemplates a method of ameliorating one or more of the symptoms of sepsis by administering to a patient in need of such therapy a therapeutically effective amount of an anti-CD14 antibody.

The phrase "therapeutically effective amount" is used herein to mean an amount sufficient to prevent, and preferably reduce by at least about 30 percent, more preferably by at least 50 percent, most preferably by at least 90 percent, a clinically significant increase in the plasma level of TNF. Preferred therapeutically effective amounts for the agents used herein as active ingredients include those described in Section C. A clinically significant increase in the plasma level of TNF is an increase to at least about 25 pg/ml. Methods for determining the plasma TNF levels are well known in the art, particularly preferred methods being those described herein.

It should be noted that levels of TNF in normal healthy humans or in laboratory animals are estimated to be no more than about 10 pg/ml, a value that is at the limit of detection by the most sensitive assays for TNF. Michie et al., *New Eng. J. Med.* 318:1481–1486 (1988); Mathison et al., *J. Clin. Invest.* 81:1925 (1988) and Waage et al., *Laucet,* 1:355–357 (1987). Following exposure to LPS, the levels of TNF have been shown to rise 10–20 fold to levals of up to 400 pg/ml (*vide supra*). Recently a good correlation has been shown between serum TNF levels and fatal outcome in infection with gram-negative, LPS-containing meningococcal bacteria. Waage et al., *Lancet,* 1:355–357 (1987). Further in animal models of sepsis with subhuman primates similar increases in TNF were noted and these changes were directly correlated with lethality. Tracey et al., *Nature,* 330:662–664, (1987).

In another embodiment, the method comprises administering to a patient in need of treatment or at risk for Sepsis a therapeutically effective amount of an anti-CD14 antibody, preferably an amount sufficient to inhibit LPS-induced TNF secretion in vivo by cells, such as cells of the monocyte/macrophage lineage, preferably monocyte derived macrophages.

Preferably, the anti-CD14 antibody used in a therapeutic method of this invention is an affinity purified polyclonal antibody. More preferably, the antibody is a monoclonal antibody (mAb). In addition, it is preferable for the anti-CD14 antibody molecules used herin be in the form of Fab, Fab', F(ab')$_2$ or F(v) portions of whole antibody molecules.

Preferred monoclonal antibodies useful in practicing the present invention are those capable of being produced by a hybridoma such as 60*b* described in Ashman, et al., *Blood,* 69:886–892, 1987, and most preferably by 3C10 (deposit number TIB22B at American Type Culture Collection, Rockville, Md.), described in Van Voorhis, et al., *J. Exp. Med.,* 158:126–145, 1983, and the like. While mAbs 60*b* and 3C10 can be produced by hybridoma culture, the invention is not so limited. Also contemplated is the use of mAbs produced by an anti-CD14 immunoglobulin expressing nucleic acid cloned from a hybridoma such as 60*b* and/or #C10. That is, the nucleic acid expressing the anti-CD14 antibody molecules secreted by hybridoma 3C 10 or the like can be transferred into another cell line to produce a transformant. The transformant is genotypically distinct from the original hybridoma but is also capable of producing anti-CD14 antibody molecules, including immunologically active fragments of whole antibody molecules, corresponding to those secreted by the hybridoma. See, for example, U.S. Pat. No. 4,642,334 to Reading; PCT Publication No. WO 890099 to Robinson et al.; European Patent Publications No. 0239400 to Winter et al. and No. 0125023 to Cabilly et al.

Preferred monoclonal antibodies display an immunoreactivity for CD14 that is similar to that of those produced by the above-described hybridomas. As used herein, the term "immunoreactivity" in its various grammatical forms refers to the concentration of antigen required to achieve a 50% inhibition of the immunoreaction between a given amount of the antibody and a given amount of CD14 antigen. That is, immunoreactivity is the concentration of antigen required to achieve a B/B$_0$ value of 0.5, where B$_0$ is the maximum amount of antibody bound in the absence of competing antigen and B is the amount of antibody bound in the presence of competing antigen, and both B$_0$ and B have been adjusted for background. See, Robard, *Clin. Chem.,* 20:1255–1270 (1974).

In another embodiment, a therapeutic method of the present invention comprises administering a therapeutically effective amount of an anti-LBP antibody preferably an affinity-purified polyclonal antibody and more preferably a mAb. In addition, it is preferable for the anti-LBP antibody molecules used herein be in the form of Fab, Fab', F(ab')$_2$ or F$_{(v)}$ portions of whole antibody molecules. Preferably, the amount of anti-LBP antibody administered is sufficient to reduce by at least about 30 percent, preferably by at least 80 percent, an LBP-LPS complex induced clinically significant increase in the blood level of TNF in a patient displaying at least one of the symptoms of sepsis. As previously discussed, patients capable of benefiting from this method include those suffering endotoxemia as a result of a gram-negative bacterial infection. Methods for isolating LBP and inducing anti-LBP antibodies are well known in the art. See, for example Tobias et al., *J. Exp. Med.,* 164:777–793 (1986). Methods for determining and optimizing the ability of an anti-LBP antibody to inhibit the binding of LBP-LPS complexes to CD14 and thereby inhibit LBP-induced TNF secretion, are well known in the art. For instance, an anti-LBP antibody can be substituted for the anti-CD14 antibody in the assay described in Example 16.

Preferred anti-LBP antibodies useful in practicing the present invention immunologically cross-react with a peptide analog of LBP. A "LBP peptide analog" is a polypeptide capable of competitively inhibiting the binding of LPS-LBP complexes to CD14 expressed on the surface of monocyte derived macrophages. Preferred LBP peptide analogs are those shown in Table 1.

TABLE 1

| Designation | Amino Acid Residue Sequence |
|---|---|
| C16Y | CNRLNRAPQPDELY |
| Y16C | YTTPEPSELDDEDFRC |
| K16C | KRVDADADPRQYADTC |

Methods for producing polyclonal anti-polypeptide antibodies are well known in the art. See U.S. Pat. No. 4,493,795 to Nestor, et al. A monoclonal antibody, typically containing Fab and/or F(ab')$_2$ portions of useful antibody molecules, can be prepared using the hybridoma technology described in *Antibodies A Laboratory Manual,* Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with CD14 or an LBP-binding portion thereof, or LBP or a CD14-binding portion thereof.

It is preferred that the myeloma cell line be from the same species as the lymphocytes. Typically, a mouse of the strain 129 GIX$^+$is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with CD14 or LBP and their ability to inhibit LPS-induced TNF secretion using the method described in Example 16.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/1 glucose, 20 mm glutamine, and 20% fetal calf serum. An exemplary inbred mouse strain is the Balb/c.

Methods for producing monoclonal anti-polypeptide antibodies are also well known in the art. See Niman, et al., *Proc. Natl. Acad. Sci. USA,* 80:4949–4953 (1983). Typically, one or more of LBP peptide analog is used either alone or conjugated to an immunogenic carrier, as the immunogen in the before described procedure for producing anti-CD14 monoclonal antibodies. The hybridomas are screened for the ability to produce an antibody that immunoreacts with the LBP peptide analog and LBP. The ability to inhibit LPS-LBP complex binding to CD14 by mAbs demonstrating the appropriate immunologic cross-reacting is confirmed using the assay of Example 16.

In another embodiment, a therapeutic method of the present invention involves administering a therapeutically effective amount of a LBP peptide analog, preferably an analog having a sequence as shown in Table 1.

Patients at risk for or exhibiting the symptoms of sepsis are capable of benefiting from the administration of therapeutic modalities known in the art to prevent or ameliorate those symptoms. Thus, the present invention contemplates administering a therapeutically effective amount of an anti-CD14 antibody, anti-LBP antibody, LBP peptide analog, a subcombination or combination thereof, substnatially simultaneously with therapeutic administration of a modality known to prevent or treat the symptoms of sepsis. For instance, intervention in the role of TNF in sepsis, either directly or indirectly, such as by use of an anti-TNF antibody and/or a TNF antagonist, can prevent or ameliorate the symptoms of sepsis. Particularly preferred is the use of an anti-TNF antibody as an active ingredient, such as a monoclonal antibody having an immunologic specificity for TNF corresponding to that described by [Tracey et al., *Nature,* 330:662–664 (1987)].

Similarly, a therapeutic method of this invention can further include substantially simultaneous treatment with a steroid, such as cortisol, hydrocortisone and the like.

A patient exhibiting the symptoms of sepsis is usually treated with an antibiotic, typically an aminoglycoside such as gentamycin or a beta-lactam such as penicillin, cephalosporin and the like. Thus, a preferred therapeutic method includes administering a therapeutically effective amount of an anti-CD14 antibody, anti-LBP antibody, LBP peptide analog subcombination or combination thereof as described herein, substantially simultaneously with administering a bactericidal amount of an antibiotic.

The phrase "bactericidal amount" is used herein to mean an amount sufficient to achieve a bacteria-killing blood concentration in the patient receiving the treatment. The bactericidal amount of antibiotics generally recognized as safe for administration to humans is an amount well known in the art and varies, as is also well known, with the antibiotic and the type of bacterial infection being treated.

In preferred embodiments, administration of an anti-CD14 antibody, anti-LBP antibody, LBP peptide analog or combination thereof as described herein occurs within about 48 hours, preferably within about 12-36 hours, more preferably within about 2–8 hours and most preferably substantially concurrently with administration of the antibiotic.

Antibiotics useful in practicing the present invention incluse those antibiotic, antibacterial and antiseptic agents having formulations described in the Physicians' Desk Reference, Huff, B. B. ed., Medical Economics Company, Inc., Oradell, N.J. (1989). In another embodiment, the present invention contemplates administering a therapeutically effective amount of CD14, preferably a soluble portion thereof that binds LPS-LBP complexes, alone or in subcombination or combination with a therapeutically effective amount of an anti-TNF antibody, an anti-LBP antibody, and an antibiotic. The cDNA coding for CD14 and its deduced amino acid residue sequence are well known in the art. See Goyert et al, *Science,* 239:497–500 (1988), Ferrero et al., *Nuc. Acids Res.,* 16:4173 (1988), and Bazil et al., *Eur. J. Immunol.,* 16:1583–1589 (1986).

C. Therapeutic Compositions

The present invention further contemplates therapeutic compositions useful in practicing the therapeutic methods of this invention. A subject therapeutic composition includes, in admixture, a pharmaceutically acceptable excipient (carrier) and one or more of an anti-CD14 antibody, anti-LBP antibody, and LBP polypeptide analog as described herein as an active ingredient. In preferred embodiments, the composition comprises an anti-CD14 mAb capable of inhibiting the binding of LPS-LBP complexes to CD14. A preferred mAb is 60b, and more preferably is 3C10.

In another preferred embodiment, the compositions comprise an anti-LBP antibody, preferably a mAb, that inhibits the binding of LPS-LBP complexes to CD14. Particularly preferred are compositions wherein the anti-LBP antibody immuoreacts with a LBP peptide analog having a sequence shown in Table 1.

A preferred composition comprises a LBP peptide analog that acts as an antagonist to LPS-LBP complexes in binding to CD14. Preferred LBP peptide analogs for use in compositions of this invention are those having a sequence shown in Table 1.

Preferred therapeutic compositions further include an effective amount of one or more of the following active ingredients: an antibiotic, a steroid, and anti-TNF antibody and a TNF antagonist. Exemplary formulations are given below:

| Ingredient | Dose (mg/ml) |
|---|---|
| Formulation A | |
| gentamicin (sulfate) | 40 |
| Anti-CD14 (mAb 3C10) | 10 |
| sodium bisulfite USP | 3.2 |
| disodium EDTA USP | 0.1 |
| water for injection q.s.a.d. | 1.0 ml |
| Formulation B | |
| anti-TNF antibody | 10 |
| anti-CD14 (mAb 3C10) | 10 |
| sodium bisulfite USP | 3.2 |
| disodium EDTA USP | 0.1 |
| water for injection q.s.a.d. | 1.0 ml |

-continued

| Ingredient | Dose (mg/ml) |
| --- | --- |
| Formulation C | |
| gemtamicin (sulfate) | 40 |
| anti-TNF antibody | 10 |
| anti-CD14 (mAb 3C10) | 10 |
| sodium bisulfite USP | 3.2 |
| disodium EDTA USP | 0.1 |
| water for injection q.s.a.d. | 1.0 ml |

In another embodiment, the present invertium contemplates a therapeutic composition useful in treating sepsis comprised of CD14 or a LBP-binding soluble portion thereof in a pharmaceutically acceptable carrier. Preferably, the composition further includes a therapeutically effective concentration of one or more of an anti-TNF antibody, an anti-LBP antibody and an antibiotic.

The preparation of therapeutic compositions which contain polypeptides or antibody molecules as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide or antibody can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide- or antibody-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of CD14 or LPS-LBP complex binding capacity desired. Precise amounts of active ingredient required to be administered depend on the judgment of the practitioner and are peculiar to each individual. However, suitable dosage ranges are of the order of 0.1 to 20, preferably about 0.5 to about 10, and more preferably one to several, milligrams of active ingredient per kilogram bodyweight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nano molar to ten micromolar in the blood are contemplated.

As used herin, "pg" means picogram, "ng" means nanogram, "ug" means microgram, "mg" means milligram, "ul" means microliter, "ml" means milliliter, "l" means liter.

EXAMPLES

The following examples are intended to illustrate, but not limit, the present invention.

Examples 1–11 illustrate studies establishing that human cells of the monocyte/macrophage lineage bind LPS-LBP complexes via a cell surface receptor that is mobile in the plane of the membrane.

Example 12 illustrates that anti-CD14 antibodies can specifically inhibit the binding of LPS-LBP complexes to CD14.

Examples 13–15 demonstrate that CD14 specifically binds LPS-LBP complexes and that that binding induces TNF secretion from MO.

Example 16 demonstrates that anti-CD14 mAbs inhibit LPS-LBP complex induced TNF secretion in human blood.

Example 17 provides a summary and discussion of the results of Examples 1–16.

1. Reagents

LBP was purified from acute phase rabbit serum (Tobias, et al., *J. Exp. Med.,* 164:777–793 (1986)), and appeared homogeneous on silver stained gels. Anti-rabbit LBP was raised in goats. MBP was obtained from Dr. R. A. B. Ezekowitz (Boston, Mass.). Bactericidal/permeability-increasing factor (BPI) was obtained from Dr. J. Gabay (New York, N.Y.). LPS from *Salmonella minnesota (Re595* or wild type) was obtained from List Biological (Campbell, Calif.). Monoclonal antibodies (mAbs) IB4 against CCD18 and 3G8 against FcyRIII (CD16) were described in Wright, et al., *Proc. Natl. Acad. Sci. USA,* 80:5699–5703, (1983). mAb 543 against CR1 was obtained from Dr. R. Schreiber (St. Louis, Mo.), and mAbs 22 and IV.3, against FcyRI and FcyRII, were obtained from Dr. M. Fanger (Hanover, N.H.). Pyrogen-free human serum albumin (HSA) was from Armour Pharmaceuticals, and pyrogen-free PBS and DGVB++were from Whitaker Mass. Bioproducts. NHS-biotin, Sulfo-NHS-biotin, and streptavidin were from Pierce Chemical.

2. Surfaces

Tissue culture plastic surfaces were coated by incubation with 25 ug/ml protein (antibody, LBP, or HSA) or 1 (ug/ml) per microgram/milliliter LPS for 1 hour(hr) at 20 degrees C. To form immune complexes, HSA-coated surfaces were incubated with anti-HSA antiserum (1:50) for an additional 30 minutes (min). In some cases, LPS-coated surfaces were subsequently treated with 10 ug/ml LBP for 30 min at 20 C. For assays of hydrogen peroxide production, all coated surfaces were exposed to 1 milligram per milliliter (mg/ml) HSA for 1 hr prior to the addition of phagocytes. Coated surfaces were carefully washed with pyrogen free PBS before the assays.

3. Cells

Monocyte-derived macrophages (MO) were obtained by culturing purified human monocytes in Teflon beakers for 3–10 days as described by Wright, et al., *J. Exp. Med.,* 156:1149–1164, (1982). Monolayers of fresh monocytes were obtained by allowing peripheral blood mononuclear cells to adhere to protein-coated plastic for 45 min at 37 C. PMN were purified from fresh blood by the method of English, et al., *J. Immunol. Methods*, 5:249, (1974). T cells, purified by rosetting with erythrocytes, were obtained from J. Ming (Rockefeller U.). Human umbilical vein endothelial cell monolayers (Lo, et al., *J. Exp. Med.,* 169:1779–1793, (1989)) were obtained from Dr. S. K. Lo (Rockefeller U.).

Sheep erythrocytes (E) were coated with IgG (EIgG) or IgM (EIgM) as described by Wright, et al., *J. Exp. Med.,* 156:1149–1164, (1982).

C3bi was deposited on EIgM by incubating $2-10 \times 10^8$ EIgM in 1 ml of 10% C5-deficient human serum (Sigma) for 30 min at 37 C. The erythrocytes were then washed and incubated for 10 min at 0 C. in a buffer containing 2.5 mM ethylenediametetracetate (EDTA). The resulting EC3bi bore no C3b as assayed by EDTA-resistant resetting with MO.

E were coated with LPS as described by Wright, et al., *J. Exp. Med.,* 164:1876–1888, (1986). The amount of LPS used in the preparation was varied to yield $ELPS^{hi}$ (1–10 ug/$4 \times 10^7$E) or $ELPS^{lo}$(0.2–1 ug/$4 \times 10^7$E). $ELPS^{lo}$ were coated with LBP by incubating equal volumes of $ELPS^{lo}$ ($10^8$/ml) and LBP (10 ug/ml) for 20 min at 37 C. The resulting LBP-coated ELPS (ligand-coated E) were washed and used immediately.

For some studies E were also coated with LBP by an alternative method. E were first biotinylated by incubating $5 \times 10^8$ E with 250 ug Sulfo-NHS-biotin for 20 min at 5 C. in 0.1 M sodium carbonate pH 9.2, and LBP was biotinylated by incubating 50 ug LBP with 5 ug Sulfo-NHS-Biotin and dialyzing against PBS. The biotinylated protein was then linked to the biotinylated E through a streptavidin bridge. $10^8$ washed, biotinylated E (EB) were incubated with 10 ug Streptavidin for 30 min at 20 C. to yield avidin coated erythrocytes (EBAV). Preliminary experiments using fluoresceinated streptavidin showed that the EBAV were uniformly and intensely fluorescent, and no agglutination could be seen. $2.5 \times 10^7$ washed EBAV were incubated with 2.5 ug of biotinylated LBP for 30 min at 20 C. to yield EBAV-LBP.

*Salmonella typhimurium* LT2 Gal E was grown in the presence or absence of galactose to yield cells with a complete or truncated LPS, respectively. Wright, et al., *J. Exp. Med.,* 164:1876–1888, (1986). Exponentially growing cultures were washed, labelled with fluorescein, and adjusted to $2 \times 10^8$/microliter(ul) in PBS as previously described. Wright, et al., *J. Exp. Med.,* 164:1876–1888, (1986).

4. Assays

Agglutination of LPS-coated erythrocytes (Example 3) was measured by shaking $10^6$ $ELPS^{hi}$ in 10 ul of diluted LBP for 30 min at 21 C. in a round bottom microtest plate. Agglutination was read from the settling pattern.

Binding of ligand-coated E (Example 3) to MO was measured as described by Wright, et al., *J. Exp. Med.,* 156:1149–1164, (1982). Briefly, Terasaki tissue culture plates were coated with HSA or other proteins (Example 2), and monolayers of MO were established by incubating 5 ul of cells ($0.5 \times 10^6$/ml in PBS containing 3 mM glucose, 0.5 mg/ml HSA, and 0.3 u/ml aprotinin (Sigma), for 45 min at 37 C. Ligand coated E and the indicated proteins were added to the monolayers. E were allowed to settle for 10 min at 0 C., then the plate was warmed to 37 C. for 15 min. Unattached E were removed by washing and attachment was scored by phase contrast microscopy. Binding of fluoresceinated *Salmonella* was assessed by a similar method employing a 15 min incubation at 37 C. as described by Wright, et al., *J. Exp. Med.,* 164:1876–1888, (1986). Results are reported as attachment index, the number of E or bacteria per 100 MO. Phagocytosis of ligand-coated E was measured by similar methods (Wright, et al., *J. Exp. Med.,* 156:1149–1164, (1982)), with the exception that incubation of MO with the E was for 45 min at 37 C., and uningested E were lysed by brief exposure to hypotonic medium before scoring the wells.

5. LBP Binds To LPS Inserted IntoErythrocyte Membranes

Addition of as little as 0.5 ug/ml of LBP to $ELPS^{hi}$ caused agglutination. Since LPS partitions into the membrane of E by hydrophobic interactions with phospholipids, this observation suggests that LBP recognizes the exposed hydrophilic portion of lipid A, and that LBP has the potential to form multimers. The ELPS were not strongly agglutinated and could be disrupted by gentle pipetting.

6. LBP Enhances Binding Of ELPS And Salmonella to Macrophages

Gram-negative bacteria and LPS-coated erythrocytes bind to MO through an interaction of LPS with members of the CD18 complex of receptors on leukocytes. Wright, et al., *J. Exp. Med.,* 164:1876-1888, (1986). The ability of LBP to perturb that interaction was therefore examined. Initial studies employed E prepared with high levels of LPS. These $ELPS^{hi}$ bound avidly to MO, and the addition of LBP slightly enhanced binding. To examine the nature of this enhancement, E were prepared with low levels of LPS. Monolayers of MO were incubated with $ELPS^{lo}$ in the presence or absence of 5 micorgrms (ug) per millileter (ml) LBP. $ELPS^{lo}$ were poorly bound by MO, but the addition of LBP caused a dramatic enhancement of binding (FIG. 1). Enhanced binding was dose dependent with a maximal effect at 1 ug/ml LBP. The specificity of this effect is indicated by the observation that another acute phase reactant, mannose binding protein, did not affect binding of $ELPS^{lo}$ to MO (FIG. 1) at concentrations as high as 100 ug/ml; another LPS-binding protein, BPI, did not affect binding at concentrations as high as 10 ug/ml; and polyclonal anti-LBP antiserum (1:200) caused a 20-fold reduction in the rosetting of $ELPS^{lo}$ cause by LBP.

Figure 2:
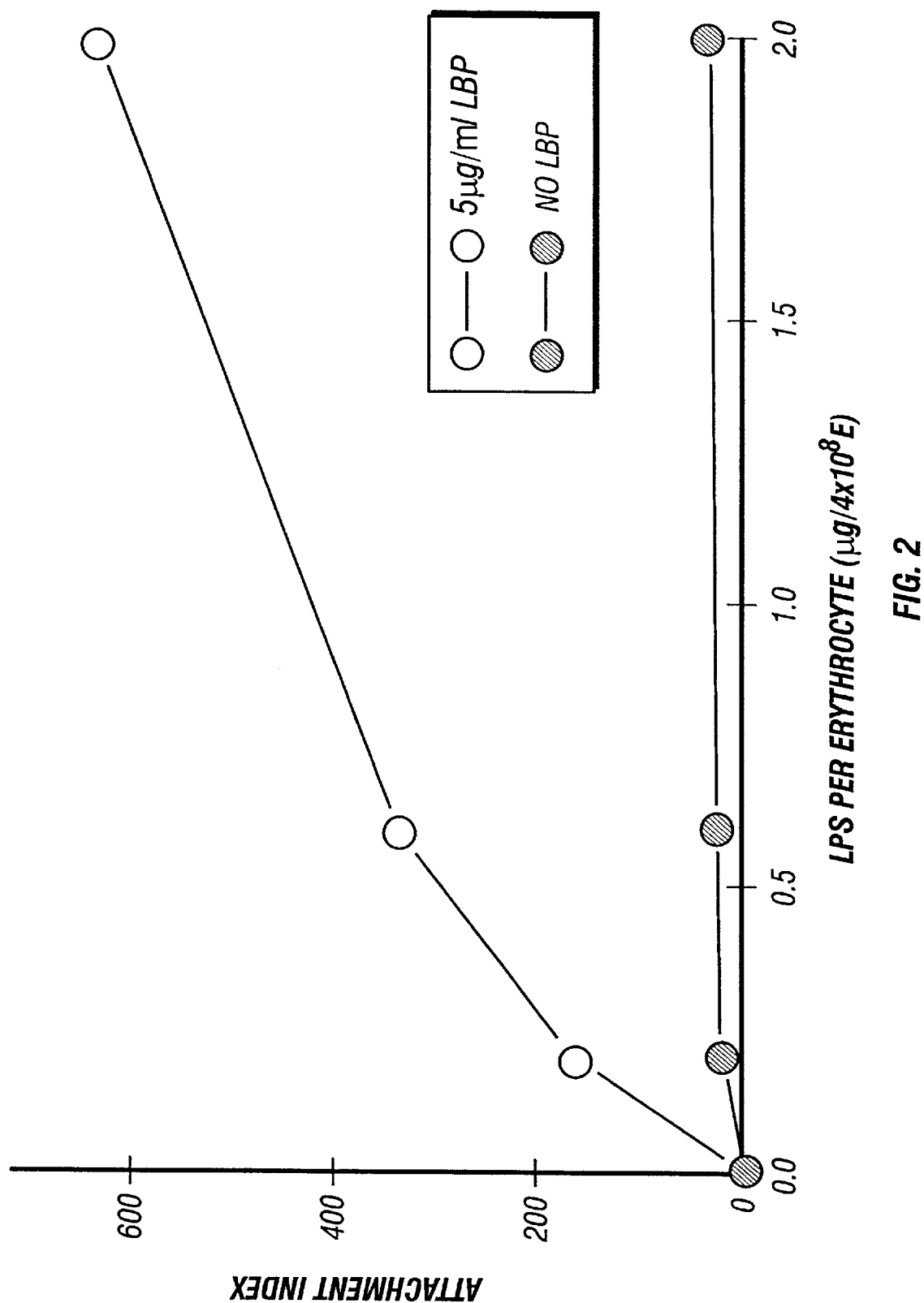
FIG. 2 illustrates LBP-dependent binding of ELPS to MO depends on the density of LPS in the E membrane. ELPS were prepared with varying doses of LPS then incubated with monolayers of MO in the presence or absence of 5 ug/ml LBP. Results are representative of 4 separate experiments.

The capacity of LBP to enhance interaction of ELPS with MO was also dependent on the amount of LPS in the erythrocyte membrane (FIG. 2). LBP could effectively mediate binding of E prepared with amounts of LPS20–100 fold less than the amount needed to sustain a dirct interaction between ELPS and MO.

Strains of gram-negative bacteria that express a truncated LPS (rough strains) are avidly bound by MO, but smooth strains, with a complete LPS, are bound poorly. Wright, et al., *J. Exp. Med.,* 164:1876–1888, (1986). Because LBP binds equally well to both smooth and rough LPS, [Tobias, et al., *J. Biol. Chem.,* 264:10867–10871, (1989)], the ability of LBP to opsonize smooth *Salmonella* was examined. As illustrated by the data shown in Table II, the addition of LBP caused a dramatic enhancement in the binding of smooth *Salmonella* to MO.

TABLE II

LBP Enhances Binding Of Salmonella To MO[1]
Attachment Index

|  | smooth S. typhimurium | rough S. typhimurium |
|---|---|---|
| −LBP | 273 | 1,096 |
| +LBP | 1,661 | 2,109 |

[1]Smooth and rough form preparations of S. typhimurium LT2 were obtained by growing GalE mutants of this strain in the presence or absence of galactose as described by Wright, et al., J. Exp. Med., 164:1876–1888, (1986). The binding of bacteria to monolayers of macrophages was then measured in the presence of absence of 2.5 μg/ml LBP. Addition of LBP caused a 5.9 ± 1.9 (n − 4) fold enhancement in the binding of smooth bacteria to MO.

[1]Smooth and rough form preparations of S. typhimurium LT2 were obtained by growing Gal E mutants of this strain in the presence or absence of galactose as described by Wright, et al., J. Exp. Med., 164:1876–1888, (1986). The binding of bacteria to monolayers of macrophages was then measured in the presence of absence of 2.5 ug/ml LBP. Addition of LBP caused a 5.9±1.9 (n-4) fold enhancement in the binding of smooth bacteria to MO.

Table II illustrates that the addition of LBP also enhanced the binding of rough Salmonella, but the effect appeared less dramatic than that seen with smooth S. typhimurium due to the avid binding of unopsonized bacteria. Thus, LBP can enhance the interaction of live, intact bacterium with MO.

7. MO Recognize Complexes Of LBP With LPS

In Example 6, LBP was added together with the MO and the ELPS. To determine if LBP binds to MO or ELPS, the cells were separately incubated (treated) with LBP, washed, and then combined. The results of this study are shown in Table III.

TABLE III

Pretreatment Of ELPS But Not MO With LBP Enhances Their Interaction[1]
Attachment Index

| Condition | Study 1 | Study 2 | Study 3 |
|---|---|---|---|
| no LBP | 6 | 17 | 4 |
| Pretreat ELPS$^{lo}$ | 820 | 715 | 942 |
| Pretreat MO | 5 | 21 | 16 |
| coincubate LPB, ELPS$^{lo}$ and MO | 629 | 520 | 796 |

[1]Binding of ELPS$^{lo}$ (0.2 ug/4 × 10$^8$ E) to monolayers of MO was measured as described in Example 4. ELPS$^{lo}$ or MO pretreated at 37 C with 5 ug/ml for 20 min and washed before the assay. Alternatively, 5 ug/ml LBP was added during the assay of attachment.

[1]Binding of ELPS$^{lo}$ (0.2 ug/4×10$^8$ E) to monolayers of MO was measured as described in Example 4. ELPS$^{lo}$ or MO pretreated at 37 C. with 5 ug/ml for 20 min and washed before the assay. Alternatively, 5 ug/ml LBP was added during the assay of attachment.

Pre-treatment of ELPS$^{lo}$ with LBP strongly enhanced binding to MO (Table III) with a dose response curve identical to that observed in the coincubation experiments (data not shown). This result suggests that LBP associates stably with ELPS and that the surface-bound LBP is recognized by MO. Pre-treatment of MO, on the other hand, did not affect the subsequent binding of ELPS (Table III).

Figure 3:
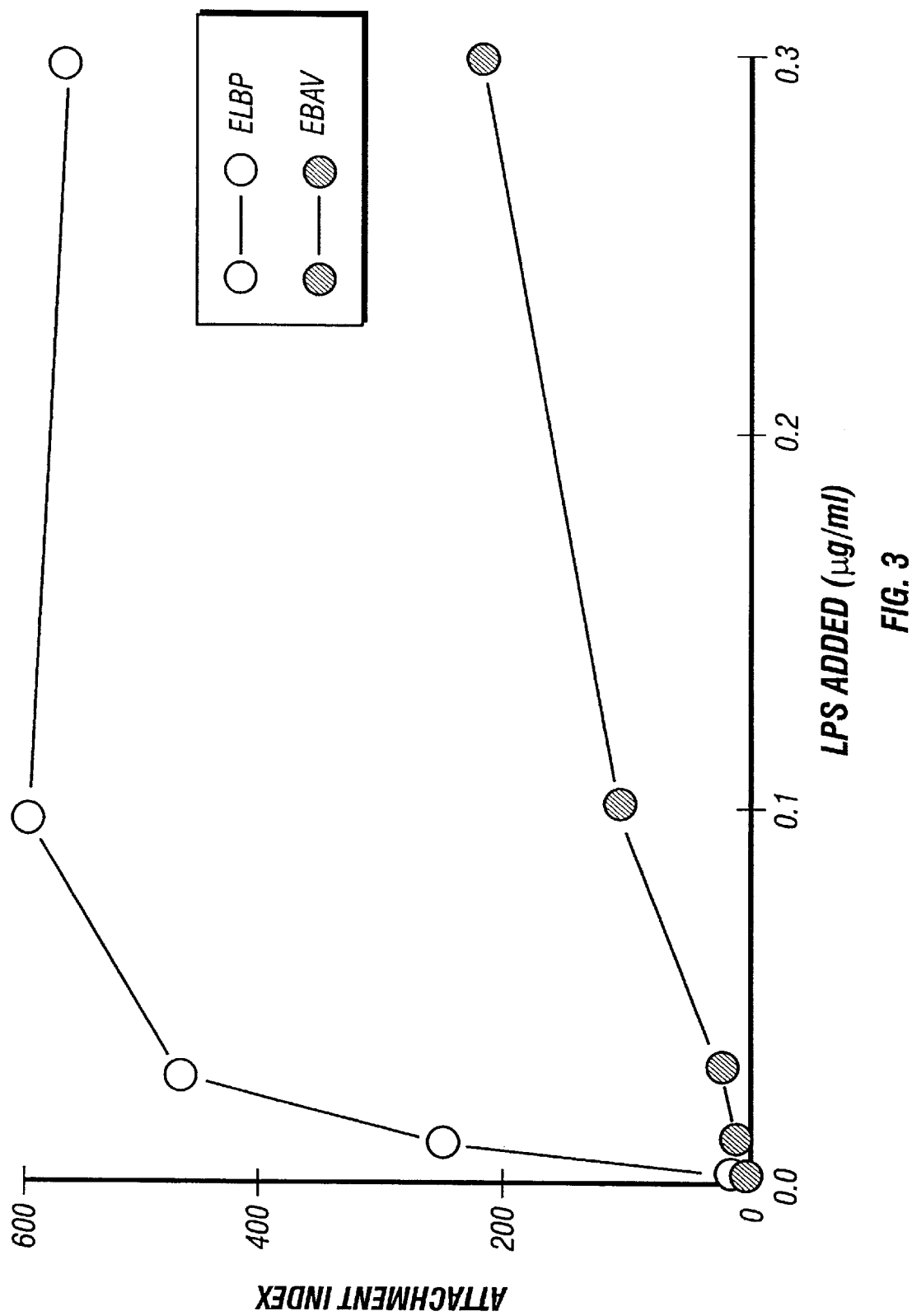
FIG. 3 illustrates that MO do not recognize LBP in the absence of LPS. E coated with biotin and streptavidin alone (EBAV) were incubated with Biotinylated LBP to yield ELBP. Both ELBP and EBAV were incubated with graded doses of LPS for 20 min at 37 C., washed, and binding to monolayers of MO was measured.

LBP on the surface of ELPS is complexed with LPS. To determine if MO bind to LBP in the absence of LPS, LBP was biotinylated and attached to streptavidin-coated erytirocytes. The resulting EBAV-LBP were not bound by MO (FIG. 3), but addition of LPS caused strong attachment of ELBP to MO. The LPS appeared to enhance adherence of EBAV-LBP by binding to LBP since the amount of LPS needed to cause attachment of ELBP was -50-fold less than needed to cause attachment of E lacking LBP (FIG. 3). Further, the LPS-treated ELBP bound avidly to CD18-deficient MO, which do not bind ELPS. Thus, LP must be complexed with LPS in order to be recognized by MO.

8. LBP Is Recognized By A Mobile Receptor Restricted To Mononuclear Phagocytes LBP-treated ELPS bound to virtually 100% of monocytes and MO, suggesting that binding activity is present on all members of these populations. To determine whether LBP interacts with other cell types, monolayers of PMN, T-cells, and umbilical vein endothelial cells were incubated with LBP-treated ELPS$^{lo}$. No binding was observed. Similarly, lymphocytes that occasionally contaminate MO preparations were never observed to bind LBP-coated E. Thus, the capacity to bind LBP-coated particles appears to be a property restricted to mononuclear phagocytes.

The existence of a specific receptor for LBP was demonstrated by allowing MO to spread on surfaces coated with complexes of LPS and LBP. Table IV illustrates that surface-bound LBP strongly down-modulated binding of LBP-treated ELPS but had no effect on the binding EIgG or EC3bi.

TABLE IV

Receptors For LBP Are Mobile In The Plane Of The Membrane[1]

| Surface | ELPS$^{lo}$LBP | ELPS$^{hi}$ | EC3bi | EIgG |
|---|---|---|---|---|
| HSA | 833 | 507 | 915 | 621 |
| HSA-anti-HSA | 795 | 455 | 1,051 | 45 |
| IB4 | 846 | 149 | 200 | 253 |
| LPS-LBP | 147 | 628 | 1,161 | 762 |

[1]Plastic surfaces were coated with HSA (500 ug/ml), mAb IB4 (25 ug/ml) or LPS (1 ug/ml) for 2 hr at 21 C and washed thoroughly. Where indicated, anti-HSA (1:40 dilution of rabbit anti-HSA antiserum) or LBP (5 ug/ml) was added and incubated for 30 min at 20 C. MO were allowed to spread on the washed, coated surfaces for 45 min at 37 C, and after an additional wash, the ligand-coated erthrocytes were added. ELPS$^{hi}$ were prepared with 3 ug LPS/4 × 10$^7$E. ELPS$^{lo}$ were prepared with 0.3 ug LPS/4 × 10$^7$E then treated with 5 ug/ml LBP as described in Example 3. Data shown are representative of four separate experiments.

[1]Plastic surfaces were coated with HSA (500 ug/ml), mAb IB4 (25 ug/ml) or LPS (1 ug/ml) for 2 hr at 21 C. and washed thoroughly. Where indicated, anti-HSA (1:40 dilution of rabbit anti-HSA antiserum) or LBP (5 ug/ml) was added and incubated for 30 min at 20 C. MO were allowed to spread on the washed, coated surfaces for 45 min at 37 C., and after an additional wash, the ligand-coated erythrocytes were added. ELPS$^{hi}$ were prepared with 3 ug LPS/4×10$^7$E. ELPS$^{lo}$ were prepared with 0.3 ug LPS/4×10$^7$E then treated with 5 ug/ml LBP as described in Example 3. Data shown are representative of four separate experiments.

The above results indicate that LBP is recognized by a molecule that is mobile in the plane of the membrane, and suggest that this receptor is different from CR3 and FcR.

9. LBP Does Not Interact With CR3 Or FcR

Because LPS is known to be recognized by CR3 and other members of the CD18 complex (LFA-1 and p150,95) (Wright, et al., J. Exp. Med., 164:1876–1888, (1986)), it appeared possible that LBP enhanced binding of ELPS by facilitating the interaction of a low amount of LPS with these receptors. Several observations, however, rule out this possibility. The results illustrated in Table V indicate that LBP caused strong binding of ELPS to monocytes isolated from two patients with a congenital deficiency of CD18. The CD18-deficient cells exhibited negligible binding of ELPS$^{hi}$ or EC3bi in parallel assays.

TABLE V

LBP Mediates Binding Of ELPS$^{lo}$ To Monocytes From CD18 Deficient Patients[1]
Attachment Index

| Subject | EC3bi | ELPS$^{hi}$ | ELPS$^{lo}$ | ELPS$^{lo}$ + LBP |
|---|---|---|---|---|
| Control 1 | 129 | 108 | 31 | 282 |
| Control 2 | 162 | 185 | 27 | 437 |
| Patient 1 | 4 | 17 | 15 | 394 |
| Patient 2 | 16 | 5 | 14 | 529 |

[1]Monolayers of monocytes from two CD18 deficient patients (CD18 deficient leukocytes respond to LPS in vitro) and two normal adult controls were incubated with EC3bi, ELPS$^{hi}$ (3 ug/4 × 10$^8$E), ELPS$^{lo}$ (1 ug/4 × 10$^8$E), and attachment index was measured. Where indicated, 2.5 ug/ml LBP was added with the ELPS$^{lo}$.

[1]Monolayers of monocytes from two CD18 deficient patients (CD18 deficient leukocytes respond to LPS in vitro) and two normal adult controls were incubated with EC3bi, ELPS$^{hi}$(3 ug/4×10$^8$E), ELPS$^{lo}$(1 ug/4×10$^8$E), and attachment index was measured. Where indicated, 2.5 ug/ml LBP was added with the ELPS$^{lo}$.

Further evidence against the participation of CD18 molecules in recognition of LBP-treated ELPS$^{lo}$ comes from experiments in which CD18 molecules were depleted from the apical surface of MO by allowing them to spread on surfaces coated with anti-CD18 mAbs. Ma IB4 down-modulated CD18 molecules as shown by the decreased binding of EC3bi and ELPS$^{hi}$, but LBP-treated ELPS$^{lo}$ bound normally to these cells (Table IV). Finally, depletion of Ca++ and Mg++ completely blocks binding of both C3bi and LPS to the CD18 complex [Wright et al., *J. Exp. Med.*, 156:1149–1164 (1982) and Wright et al., *J. Exp. Med.*, 164:1876–1888 (1986)] but binding of LBP-treated ELPS$^{lo}$ was equivalent in EDTA-containing buffers.

The participation of Fc receptors in the recognition LBP was also ruled out. Spreading of cells on an immune-complex coated surface strongly down-modulated Fc receptors as assayed by the binding of EIgG. However, the binding of LBP-coated ELPS$^{lo}$ was unaffected (Table IV). Similar studies showed that surface-bound mannose binding protein and surface-bound mAbs against FcRI, FcRII, FcRIII, and CR1 had no effect on the binding of LBP to MO. These data suggest that LBP is not recognized by CR1, CR3, FcR or mannose binding protein receptors.

10. Receptors For LBP Enhance Fc-Mediated Phagocytosis

Figure 4:
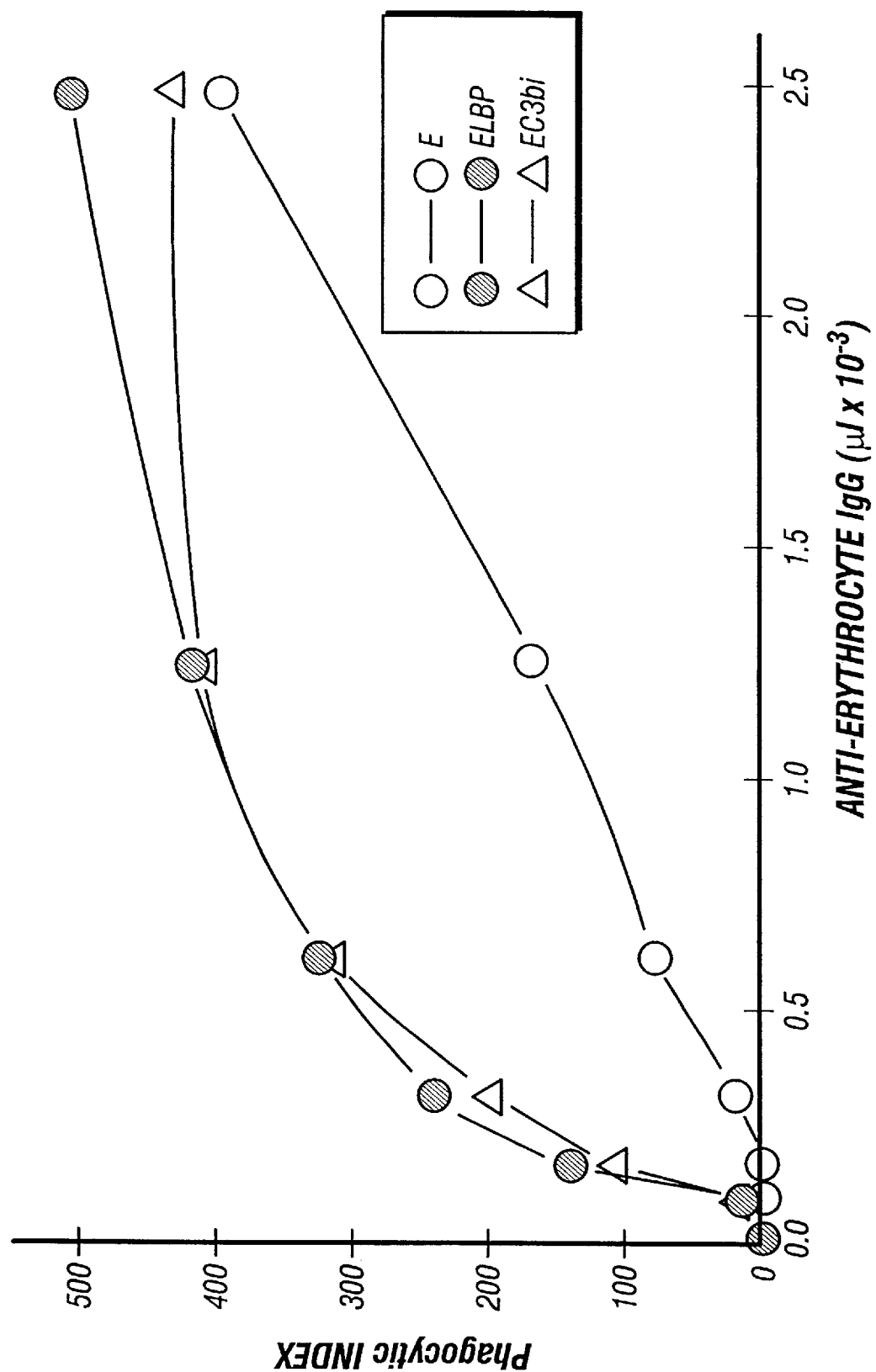
FIG. 4 illustrates that LBP enhances Fc-mediated phagocytosis. Monolayers of MO (day 5 culture) were incubated for 45 min with E, ELBP, or EC3bi in the presence of varying dilutions of anti-E-IgG. Phagocytosis of the E was determined as described in Materials and Methods. ELBP were obtained by adding 1 ug/ml LBP to ELPS$^{lo}$ (0.3 ug LPS/3×10$^7$E) during incubation with MO. Attachment of these E in the absence of anti-E IgG was as follows: E, Attachment index (AI)-O; EC3bi, AI-417; ELBP, AI-404. Results are representative of six separate experiments.

Addition of anti-E IgG caused LBP-coated ELPS$^{lo}$ to be avidly phagocytosed by MO (FIG. 4). The dose of anti-E IgG needed for half-maximal phagocytosis was 5-fold less than that needed to induce phagocytosis of uncoated E (FIG. 4). LBP thus appears to act synergistically with IgG to induce a phagocytic response. In keeping with previous reports [Ehlenberger, et al., *J. Exp. Med.*, 145:357–371, (1977)], deposition of C3bi on E also enhanced phagocytosis mediated by IgG, and the extent of this enhancement was similar to that caused by LBP (FIG. 4).

Phagocytosis mediated by LBP alone was also examined. Though LBP-coated ELPS formed florid rosettes with MO, none of the bound E were phagocytosed by either resting (FIG. 4), fibronectin-, or PMA-stimulated MO. Parallel studies showed strong fibronectin- and PMA-stimulated phagocytosis of EC3bi. A possible explanation for the absence of LBP-mediated phagocytosis is the high lateral mobility of LPS on the surface of an erythrocyte. The LPS could "cap" on the pole of the E attached to the MO, leaving insufficient ligand on the circumference of the E to guide an advancing pseudopod. To prevent such capping, biotinylated LBP was linked to biotinylated E proteins as described in FIG. 4 above. Again, none of the E bound in this way were phagocytosed by either E coated resting or PMA-bistimulate MO (Phagocytic index=0). Parallel studies showed that with biotinylated F(ab)$_2$ of an anti-CD18 mAb (IB4) were readily phagocytosed (phagocytic index-482). Thus, receptors for LBP cannot by themselves initiate phagocytosis of a coated erythrocyte.

11. Receptors For LBP Do Not Initiate An Oxidative Burst

To determine whether interaction of LBP with its receptor initiates a cytotoxic response from MO, the production of hydrogen peroxide during the interaction of MO with coated surfaces was measured.

Release of hydrogen peroxide during spreading of MO on coated surfaces was measured as described by delaHarpe, et al., *J. Immunol. Methods*, 78:323–336, (1985). Briefly, 3–4× 10$^4$ MO (day 3 or 4) were added to protein-coated tissue culture wells containing horseradish peroxidase and 2.4 nmoles of scopoletin. The plate was incubated at 37 C., and at intervals the consumption of scopoletin was measured using an automated fluorescence plate reader. Results are averaged from triplicate wells and are presented as nmoles peroxide produced per well. Addition of the control stimulant, PMA (100 ng/ml), resulted in rapid evolution of peroxide that was identical in rate and extent for all coated surfaces tested.

Figure 5:
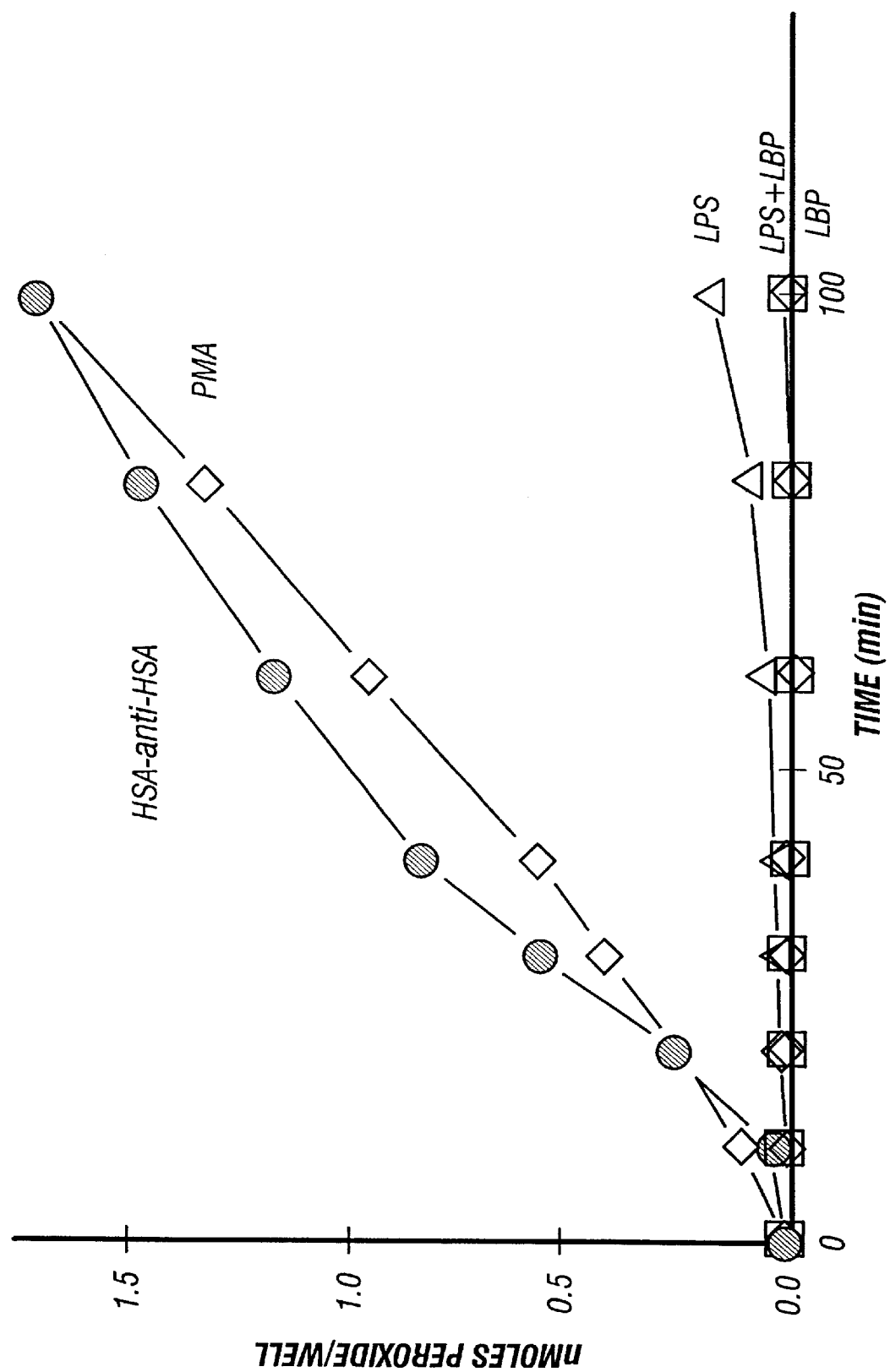
FIG. 5 illustrates that secretion of hydrogen peroxide during spreading of MO on ligand-coated surfaces. 3×10$^4$ MO (day 3 of culture) were added to coated microtitre wells and the evolution of hydrogen peroxide was measured at intervals. Brisk production of peroxide occurred during spreading on immune complexes (HSA-anti-HSA, closed circles) or in response to the soluble agonist, PMA (closed diamonds). Low but reproducible peroxide release was observed during interaction with LPS-coated surfaces (open triangles). However, spreading on LBP-coated surfaces (open square) caused no release, and coating of LPS-coated surfaces with LBP (open diamond) prevented the LPS-induced generation of peroxide. LBP did not impair the production or measurement of peroxide since MO in LBP-coated wells exhibited normal peroxide evolution in response to PMA.

FIG. 5 illustrates that MO binding to LPS-coated surfaces caused a small release of peroxide (12% of that stimulated by immune complexes or PMA). Surfaces coated with LBP, however, caused no release of peroxide above baseline. Further, addition of LBP to LPS-coated surfaces blocked the release caused by LPS, thus confirming that LBP effectively interacted with LPS in this experiment. Parallel experiments showed that spreading of MO on LBP or LPS+LBP-coated surfaces caused down-modulation of the binding of LBP-treated ELPS$^{lo}$, thus confirming that ligation of LBP receptors had occurred. Thus LBP receptors appear incapable of triggering an oxidative burst.

12. Inhibition Of LPS-LBP Complex Binding To MO By Anti-CD14 Antibodies

The ability of three anti-CD14 mAbs to inhibit the binding of LPS-LBP complexes to MO was examined. Monolayers of human MO were incubated for 15 minutes at 0 C. with mAb 3C10, 60b or 26ic at concentrations of 0 ug/ml, 0.15 ug/ml, 0.5 ug/ml, 1.5 ug/ml, 5 ug/ml, and 15 ug/ml. The ability of the monolayers to bind LBP-treated ELPS$^{lo}$ (Example 3) was assayed as described in Example 4.

Figure 6:
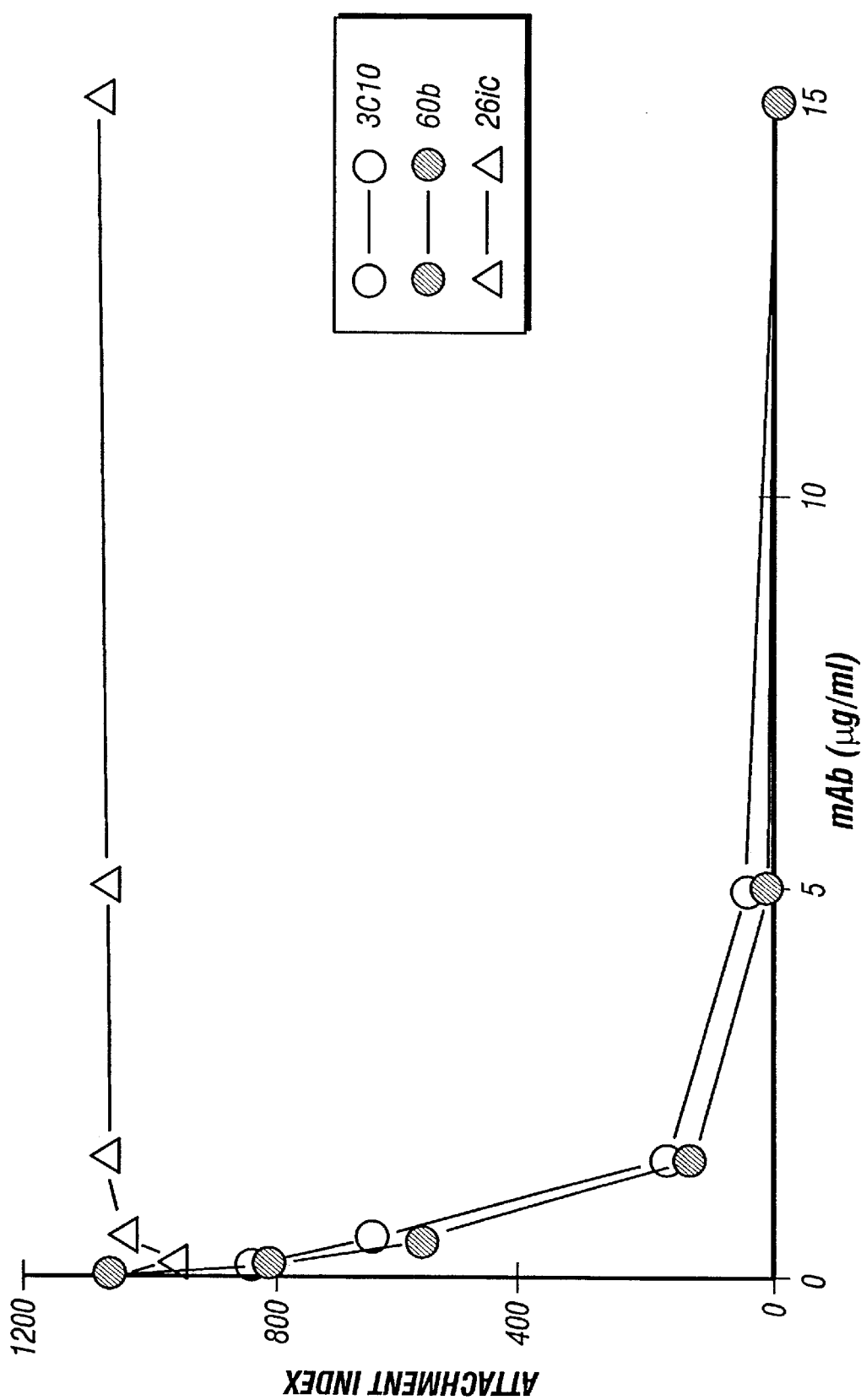
FIG. 6 illustrates the inhibition of LPS-LBP complex binding by monoclonal anti-CD14 antibodies. Monolayers of human MO were incubated for 15 min at 0 C. with the indicated concentrations of monoclonal antibodies. Erythroctyes coated sequentially with LPS and LBP were added and attachment was measured. Results are representative of three separate dose response experiments and of ten experiments performed at a fixed concentration of antibody. High concentrations of a large panel of mAbs directed against other determinants on macrophages had no effect on the binding ELBP.

The results of this study, illustrated in FIG. 6, indicate that mAbs 3C10 and 60b produced an attachment index that diminished with increasing concentration of mAb used, whereas mAb 26ic, which recognizes an epitope different from that recognized by mAbs 3C10 and 60b, failed to reduce the index below levels attained at the control mAb concentration (0 ug/ml), i.e., did not inhibit binding. Thus, mAbs 3C10 and 60b have the ability to inhibit the binding of LPS-LBP complexes to MO. The specificity of the inhibition is indicated by the observation that mAbs against CD11b, CD18, CD16 and HLA did not inhibit binding (data not shown).

Figure 7:
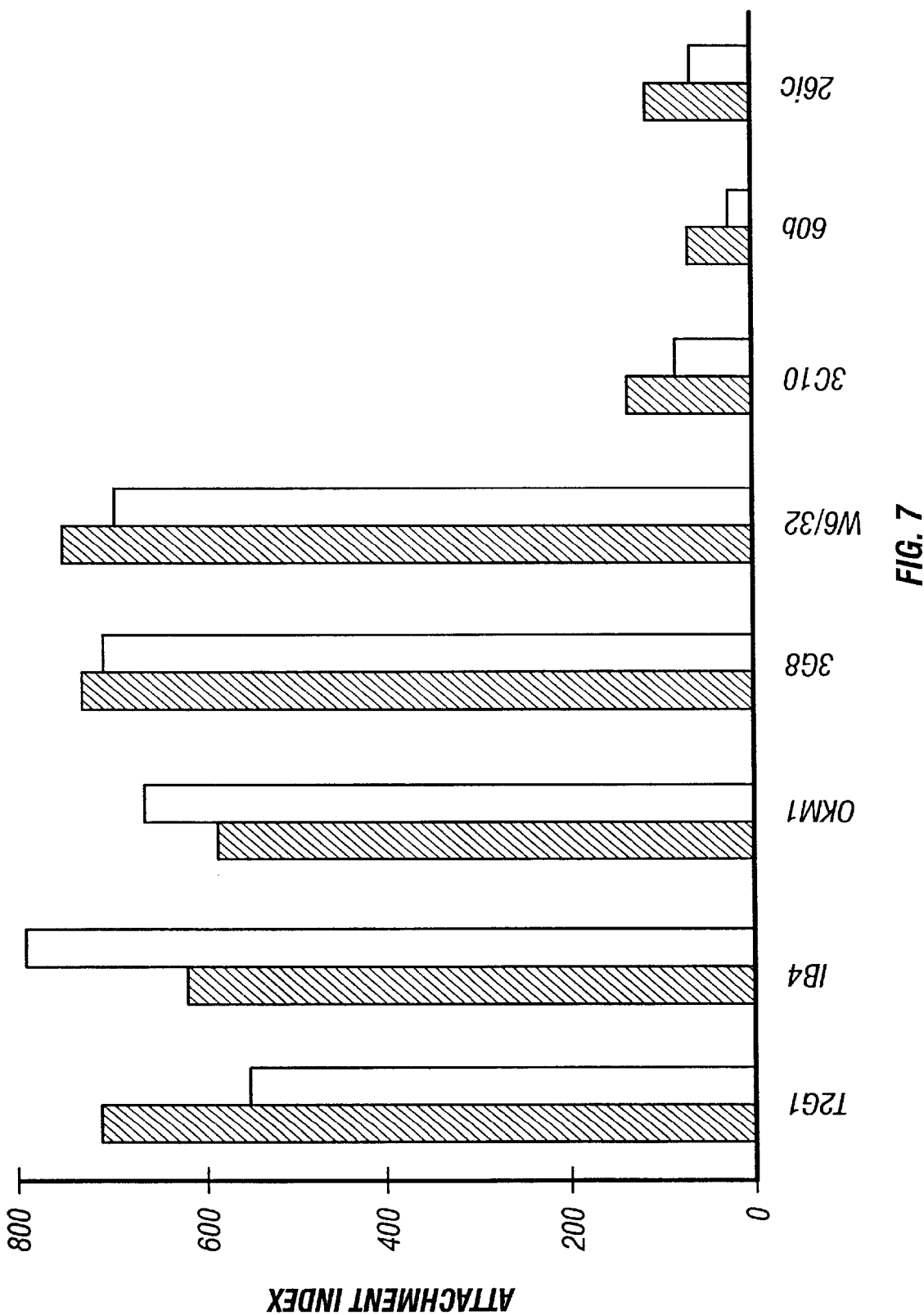
FIG. 7 illustrates that surface-bound anti-CD-14 mabs down-modulate binding of LBP-LPS complexes. Monolayers of human macrophages were established on substrates coated with 25 ug/ml of the indicated monoclonal antibodies. The cells were washed, ELPS$^{lo}$ were added, and attachment was measured.

In contrast, FIG. 7 illustrates that mAbs 26ic, 3C10 and 60b were all able to down-modulate binding of LPS-LBP complexes to MO. Monoclonal antibodies were affixed to the tissue culture plates prior to establishing the MO monolayer. This was accomplished by admixing mAb into a plate at a concentration of 25 ug protein/ml, maintaining the mAb in the plates for 60 minutes at 20 C. and then rinsing non-bound mAb from the plate prior to seeding with MO. MO attached to surfaced coated with anti-CD14 mAbs, but not other mAbs, showed decreased binding of erythrocytes coated with LPS-LBP complexes. Thus, CD14 which is redistributed to the basal surface of attached macrophages, is necessary for binding of LPS-LBP complexes. This result confirms the conclusion of FIG. 6 that CD14 serves as a receptor for LPS-LBP complexes.

13. CD14 Specifically Binds LPS-LBP Complexes

The ability of purified CD14 to specifically bind LPS-LBP complexes was examined. CD14 was immobilized on surfaces by coating them first with anti-CD14 mAbs then with a Triton X-100 extract of monocytes. $10^8$ monocytes were suspended in 1% Triton in PBS, incubated for 15 min at 0 C., then insoluble material was removed by centrifugation. The extract, which contains CD14, was applied to the antibody-coated surfaces. This procedure results in surfaces coated with CD14. In control wells bearing antibodies against antigens other than CD14, this procedure results in surfaces coated with proteins other than CD14. After thorough washing, erythrocytes coated with LPS-LBP complexes were added to the coated wells, and attachment of the erythrocytes ($ELPS^{ic}$) was documented by photography. CD14 adsorbed to the surface via mAb 26ic, an antibody to CD14 which does not block the binding site for LPS-LBP binding sites, strongly bound the coated erythrocytes. Surfaces coated with other antigens did not have this activity. Thus, the purified CD14 molecule has the ability to bind LPS-LBP complexes. This observation proves that CD14 serves as a receptor for LPS-LBP complexes.

14. LPS-LBP Complexes Induce TNF Secretion In MO

The ability of LPS in the presence of LBP, heat treated LBP, bovine serum albumin (BSA) or fetal calf serum (FCS) to induce TNF secretion in peritoneal exudate macrophages (PEM) was examined.

To produce rabbit PEM, NZW rabbits (2–2.5 kg) were given an intraperitoneal injection of 35 mineral oil (Drakeol 6VR, Pennreco, Butler, Pa.) containing 10 ug cell wall preparation from BCG (BCG Cell Walls, R-200, Ribi Inmuunochem Research, Inc. Hamilton, Mont.). Three days later, a bolus i.v. injection of 120 mg sodium pentobarbital (Western Medical Supply Inc., Arcadia, Calif.) was made, followed by aseptic lavage of the peritoneum with 500 ml ice cold RPMI-1640 supplemented with 2 mM L-glutamine, 1 mM Na pyruvate, 50 U/ 50 ug penicillin/streptomycin per ml, 10 mM Hepes, 2% fetal bovine serum and 5 U/ml heparin. The harvested cells were centrifuged (1000×G, 10 minutes, 4 C.) and resuspended in the above medium without FBS (serum-free medium). Following an additional spin and resuspension in serum-free medium, the cells were counted using a hemocytometer and plated in 150 $cm^2$ flasks at a density of $8-10 \times 10^7$ macrophages/flask. After 2 h at 37 C., 5% $CO_2$, non-adherent cells were removed from the flasks by vigorous washing and replenishment with 20 ml serum-free medium. The mineral oil induced peritoneal exudate cells, when examined using Wright's stained cytocentrifuge preparations, contained approximately 60% macrophages, 35% neutrophils and 5% lymphocytes. After plating and washing, the adherent cells were>90% macrophages. The rabbit PEM thus produced were treated with LPS isolated from Salmonella minesota Re595 (100 pg/ml) in the presence and absence of the proteins noted above for 12 hours and the cell-free supernatant assayed for TNF as described above using a modification of the L929 assay of Ruff et al., *Lymphokines*, 2: 235–242, (1981) as described in Mathison et al., *J. Clin. Invest.*, 81:1925(1988).

Briefly, L929 cells (CCL 1, American Type Culture Collection, Rockville, Md.) were maintained in RPMI 1640 supplemented with 10 mM Hepes and 10% fetal bovine serum (Hyclone, Rehatuin F.S., Reheis Chemical Co., Phoenix, Ariz.). Confluent cultures ($3-4 \times 10^7$ cells/75 cm flask) were rinsed briefly with 0.5% trypsin (TRL3, Worthington Biochemical Corporation, Freehold, N.J.) in physiologic salt solution containing 5 mM EDTA and 10 mM Hepes, pH 7.4, resuspended in fresh medium containing actinomycin D (1 ug/ml) and added to 96-well plates ($5-7 \times 10^4$ cells/well). After 2 hours in culture, serially diluted samples were added to the wells and the plates were incubated overnight (5% $CO_2$, 37° C.). Following microscopic evaluation, the medium was decanted, and the wells were filled with a solution of 0.2% crystal violet, 10% formalin and 0.01 M phosphate, pH 7–7.5 for 5 m, washed thoroughly with water and dried. The degree of lysis was quantitated spectrophotometrically (550 nm) using a Bio-Tek Model EL310 plate reader (Bio-Tek Instruments, Inc., Burlington, Vt.) interfaced with an IBM-PC computer. Assay results were expressed as U/ml, with one unit (U) defined as the amount of TNF resulting in lysis of 50% of the cells.

Routinely, 8–12 plates were set up per assay. Each plate included two laboratory standards, conditioned medium from Re595 LPS-treated RAW 264.7 cells ($6 \times 10^3$ U/ml) and conditioned medium from Re595 LPS-treated rabbit PEN ($1.3 \times 10^3$ U/ml). These standards, in turn, were calibrated against human recombinant TNF (Cetus Corporation, Emeryville, Calif., $2 \times 10^7$ U/mg) and assay results were normalized accordingly. Samples were assayed in quadruplicate, and a coefficient of variation (SD/mean) of 0.12±0.08 (SD) was observed. Using this assay, as little as 10 pg/ml of rabbit macrophage-derived TNF (specific activity $1 \times 10^8$ U/mg) could be detected. However because serum concentrations greater than 10% caused nonspecific rounding and loss of adherence of the L929 cells, the lower limit of detection of rabbit TNF in serum was 20 U/ml (corresponding to 0.2 ng TNF/ml).

Figure 8:
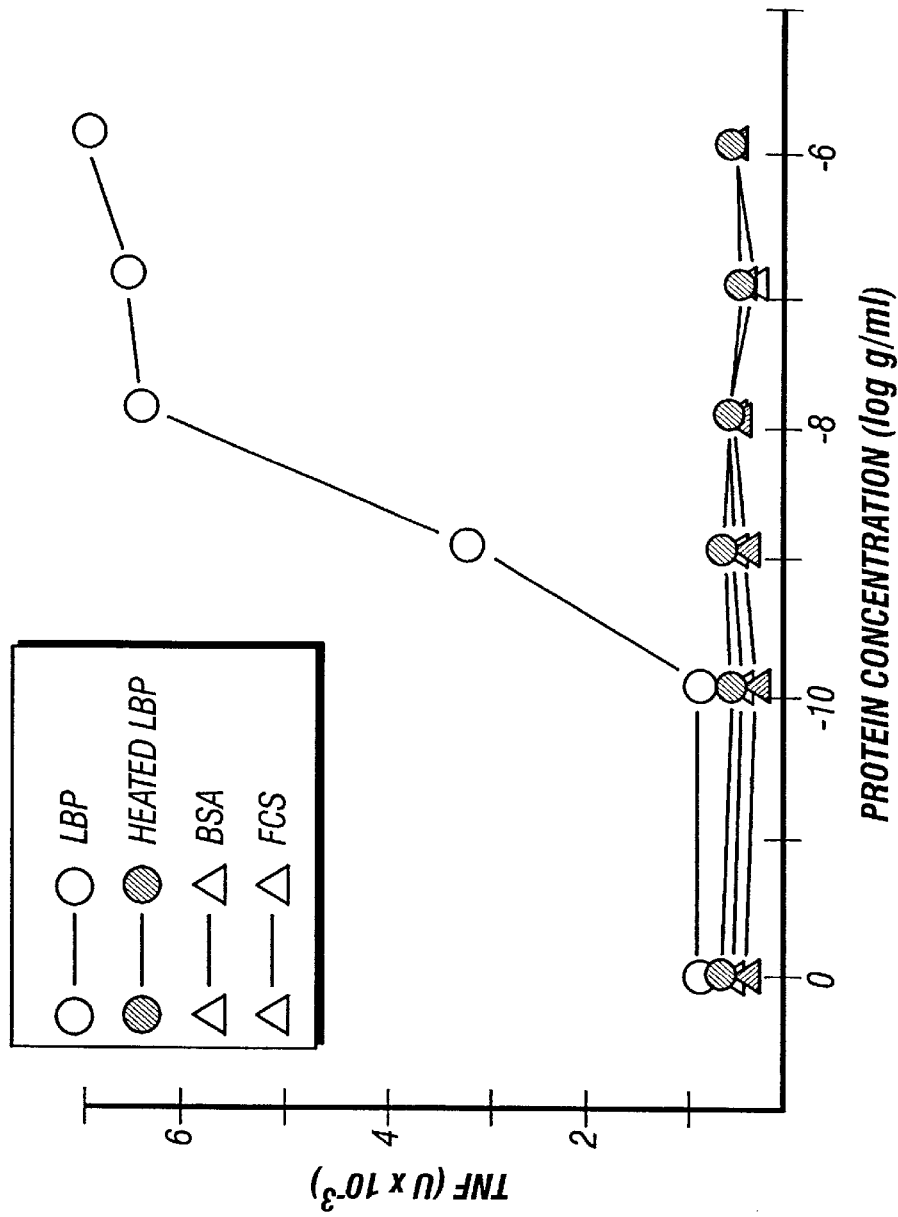
FIG. 8 illustrates that native LBP is required for LPS to induce TNF production. Rabbit peritoneal exudate macrophages (PEM) were challenged with LPS in the presence of the indicated concentrations of native LBP (LBP), heated (dentured) LBP, bovine serum albumin (BSA) or fetal calf serum (FCS). The amount of TNF produced by the challenged PEM was then determined.

The results of this study, shown in FIG. 8, demonstrate that TNF is only produced if both LPS and active LBP are present. Re595 LPS is from a rough strain of Salmonella; identical results are obtained if LPS isolated from smooth strain organisms is used such as LPS from E. coli 0111 :B4 indicating the generality of the effects observed here.

15. The Binding Of LPS TO LBP Protects LBP from Trypsin Cleavage

Figure 9:
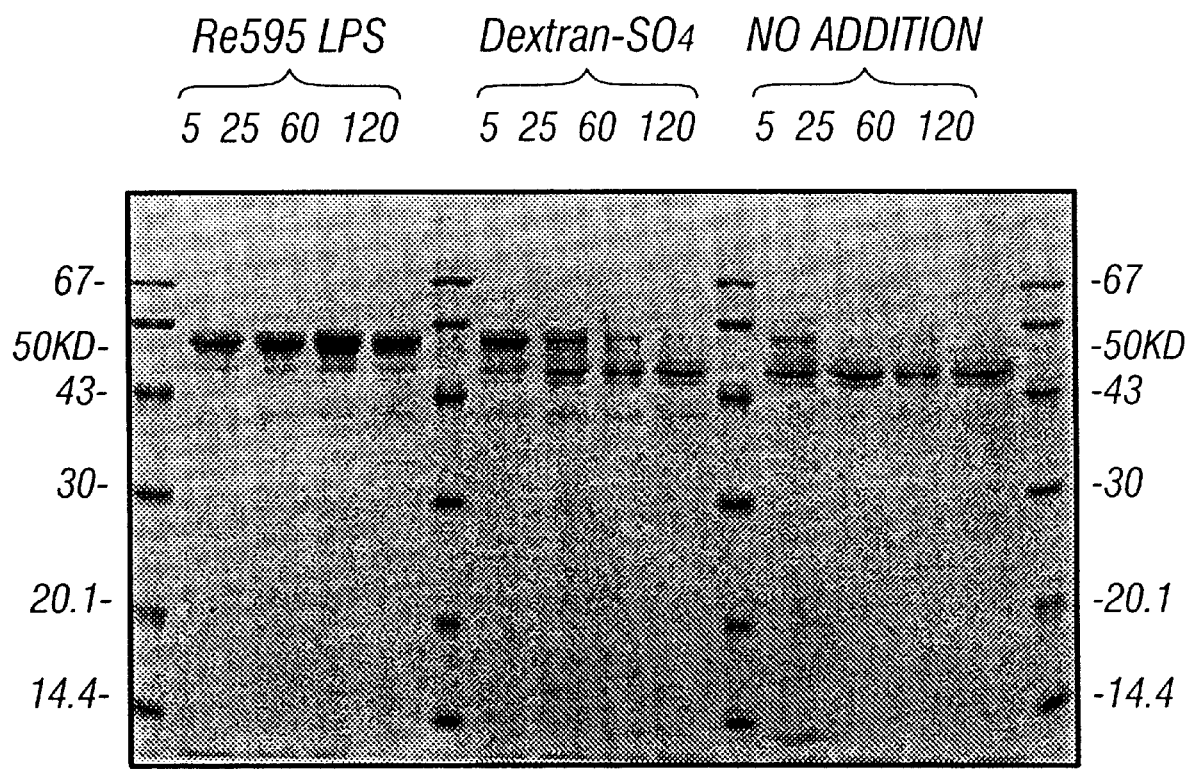
FIG. 9 illustrates the susceptibility of LBP to tryptic digestion in the presence or absence of a ligand to which it binds, i.e., Re595 LPS. Molecular weight markers (Pharmacia, Piscataway, N.J.; catalog No. 17-0446-01; phosphorylase B at 94 kilodaltons (kD), bovine serum albumin at 67 kD, ovalbumin at 43 kDa, carbonic anhdrase at 30 kD, soybean trypsin inhibitor at 20.1 kD and alpha lactalbumin at 14.4 kD.) appear in lanes adjacent to those containing LBP. The results suggest that LBP binding to LPS results in a conformational change in LBP that may account for its ability to bind CD14 only when present as part of an LPS-LBP complex.

Samples containing LBP at a final concentration of 0.3 mg/ml in a buffer containing 50 mM HEPES, 10 mM EDTA pH 7.4 were prepared. To one sample was admixed LPS to a final concentration of 0.125 mg/ml. To the second sample was admixed dextran sulfate to a final concentration of 0.125 mg/ml. Subsequently, trypin was admixed to all three samples to a final concentration of 2 ug/ml. Aliquots were removed from the trypsin-treated samples at time intervals of 5, 25, 60 and 120 minutes while being maintained at 37 C. The aliquots were then analyzed by sodium dodecyl sulfate polyacrylamide gel electrophoresis (SDS-PAGE) using 12% gels. The results of this study, shown in FIG. 9, indicate that the binding of LPS by LBP protects LBP from enzymatic degradation. LPS may protect LBP by either inducing a conformational change in LBP that prevents cleavage or sterically hindering access to the cleavage site.

16. Anti-CD14 Monoclonal Antibodies Inhibit LPS-LBP Complex Induced TNF Production In Whole Human Blood The ability of anti-CD14 mAbs to inhibit TNF secretion by MO in human blood was examined using the TNF-induced cytotoxic activity assay described by Espevik et al., *J. Immunol. Meth.*, 95:99–105, (1986). Briefly, whole human blood anticoagulated with heparin was prepared and incubated with mAb 3C10, 60b or IB4 at a final concentration of 1 ug/ml at 37 C. for 30 minutes. Subsequently, the cells were incubated with Re595 LPS at a final concetration of 0, 0.01, 0.1, or 1.0 ng/ml at 37 C. for 12 hours in a humidified, 10% $CO_2$ incubator. Plasma was then collected from each sample and examined for the presence of TNF.

For these studies it was not necessary to add additional LBP since constitutive levels of LBP in blood of healthy subjects is estimated to be 100–250 ng/ml. Tobias et al., *J. Exn. Med.* 164:777 (1986) and Tobias et al., *Infect. Immun.* 50:73–76 (1985). Based on estimates of the affinity of LPS for LBP Tobias et al., *J. Biol. Chem.* 264:10867–10871 (1989) the constitutive levels of LBP are more than sufficient to bind all of the added LPS.

WEHI clone 13 cells were obtained from T. Ezpevik at University of Trondheim, Norway and cultured in RPMI 1640 culture media (Gibco) containing 10% FCS, 0.1 mM glutamine and 30 ug/ml gentamicin. The cells were seeded in microtiter plates at a concentration of $2 \times 10^4$ cells per well in 100 microliters (ul) of RPMI 1640 culture medium. Samples of 5 to 50 microliters (ul) of MO culture supernatant was then admixed to the WEHI clone 13 cell growth media and incubated for 20 hr at 37 C. Subsequently, 10 microliters of MTT tetrazolium (M-2128 Sigma Chemical Company, St. Louis, Mo.) at a concentration of 5 mg/ml in PBS was added to each microtiter plate well and the wells were further incubated for 4 hr at 37 C. After aspirating 100 microliters of the supernatant from the wells, 100 microliters isopropanol with 0.04 N HCL was added to each well. After dissolving the dark blue formazan crystals, the plates were read on a microtiter plate reader, using a test wavelength of 570 nm and a reference wavelength of 630 nm.

Percentage of dead target cells was determined as follows:

$$= 100 - \frac{\text{optical density in wells with } CF/TNF}{\text{optical density in control wells}} \times 100$$

The percentage of dead cells obtained in the experimental cultures was then compared to the percentage obtained from various known dilutions of TNF to determine the corresponding TNF concentration of each experimental culture. The results of this study are shown in Table VI.

TABLE VI

Effect of Monoclonal Antibodies on LPS-Induced TNF Production in Whole Human Blood

| [Re595 LPS], ng/ml | Antibody[1] | [TNF], U/ml[2] |
|---|---|---|
| — | — | <0.5 |
| 0.01 | — | <0.5 |
| 0.1 | — | 4.8 |
| 1.0 | — | 39 |
| — | 3C10 | <0.5 |
| 0.01 | 3C10 | <0.5 |
| 0.1 | 3C10 | <0.5 |
| 1.0 | 3G10 | 3 |
| — | 60b | <0.5 |
| 0.01 | 60b | <0.5 |
| 0.1 | 60b | 2 |
| 1.0 | 60b | 12 |
| — | 1B4[3] | <0.5 |
| 0.01 | 1B4 | 2 |
| 0.1 | 1B4 | 13 |
| 1.0 | 1B4 | 40 |

[1]All monoclonal antibodies added at a final concentration of 1 ug/ml.
[2]TNF assays performed with the WEHI clone 13 assay using recombinant TNF having a specific activity of $2 \times 10^7$ units (u) per mg as a standard.
[3]An Anti-CD18 mAB.

[1]All monoclonal antibodies added at a final concentration of 1 ug/ml.
[2]TNF assays performed with the WEHI clone 13 assay using recombinant TNF having a specific activity of $2 \times 10^7$ units (u) per mg as a standard.
[3]An Anti-CD18 mAB.

From Table VI it can be seen that LPS induced TNF production in whole human blood increases with increasing concentration of LPS. In addition, it can be seen that LPS-LBP complex induced TNF production was significantly inhibited by anti-CD14 monoclonal antibodies 3C10 and 60b, while the anti-CD18 IB4 monoclonal antibody produced no significant inhibition of TNF production. Similar experiments were performed with LPS isolated from the smooth form bacteria E. coli 0111:B4 indicating the generality of the effect on LPS preparations with varying carbohydrates content but containing conserved lipid A structures.

The TNF specificity of the cytotoxic activity found in the whole blood was established using a polyclonal goat anti-human TNF IgG antibody as described by Mathison et al., *J. Clin. Invest.*, 81:1925(1988). This antibody completely neutralized all of the cytotoxic activity found in the samples of LPS-treated whole blood.

17. Discussion of the Results of Examples 1–16

The foregoing demonstrates that LBP functions as an opsonin because it binds bacteria and facilitates their binding and phagocytosis by macrophages. It is believed that while LBP binds LPS through a domain which is homologous with the LPS-binding domain of BPI, the attachment of LBP to cells is mediated by a domain unique to LBP.

LBP on the surface of LPS-coated particles is recognized by a specific receptor, CD14, whcih on MO is mobile in the plane of the membrane. LBP-coated particles bind to CD14-expressing cells, such as MO, but not other blood cells. The binding activity on the apical surface of MO is depleted by spreading of cells on substrates coated with LBP-LPS complexes. The receptor for LBP, CD14, is distinct from other opsonic receptors since surface-bound antibodies to CR1, CR3, and FcR did not reduce the binding of LBP-coated particles.

As an opsonin LBP promotes clearance of sepsis-inducing infectious agents, such as gram-negative bacteria. However, during sepsis bacteriolysis may occur, either through the action of endogenous lytic mechanisms including complement and degradative enzymes or following antibiotic treatments. Lysis leads to the systemic release of LPS causing increases in blood levels of LPS. Since these levels are estimated to be between 1–1000 pg LPS/ml there is sufficient LBP present to form high-affinity LPS-LBP complexes. [Sturk et al., in *Detection of Bacterial Endotoxins with the Limulus Amebocyte Lystate Test.* eds. Watson, S. W. Allan R. Liss, N.Y. 1987:371–385.] van Deventer, S. J. H. Lancet 1:605–608 (1988), et al. LPS-LBP complexes bind to CD14 on cells of the macrophage/monocyte lineage and initiate rapid synthesis and release of the monokine, TNF and thereby contribute significantly to the development of the full-blown sepsis syndrome.

The classical opsonin, IgG, facilitates the binding of IgG-coated particles, their phagocytic engulfment, and the release of toxic compounds such as hydrogen peroxide. The other classical opsonin, C3, facilitates principally the binding of C3-coated particles. Phagocytosis by unstimulated MO is observed only if the C3-coated particles also bear IgG (Ehlenberger, et al., *J. Exp. Med.,* 145:357–371, (1977)), and the evolution of hydrogen peroxide is not initiated. Wright, et al., *J. Exp. Med.,* 158:2016–2023, (1983).

The opsonic activity LBP most closely resembles that of C3. LBP-coated particles are avidly bound by MO, but binding does not initiate phagocytosis or release of hydrogen peroxide (FIG. 5). LBP also acts like C3 in that it enhances phagocytosis of particles coated with low amounts of IgG (FIG. 4). The opsonic effect of LBP differs from that of C3 in only one respect. While complement proteins may initiate phagocytosis if MO are treated with an ancillary stimulus such as PMA (Wright, et al., *J. Exp. Med.,* 156:1149–1164, (1982)) or fibronectin (Wright, et al., *J. Exp. Med.,* 158:1338–1343, (1983), LBP does not mediate phagocytosis even in such optimally stimulated cells.

By acting as an opsonin, LBP limits the spread of gram negative bacteria in an animal. The appearance of LBP during the acute phase makes it well suited to combating infection, and it is therefore believed that LBP represents a defense mechanism against infectious agents such as gram negative bacteria.

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. A method of ameliorating sepsis in a patient, which method comprises administering a therapeutically effective amount of an anti-CD14 antibody to said patient.

2. The method of claim 1, wherein the anti-CD14 antibody is a polyclonal antibody.

3. The method of claim 1, wherein the anti-CD14 antibody is a monoclonal antibody.

4. The method of claim 3, wherein the monoclonal antibody is produced by hybridoma ATCC™ TIB22B or a transformant cell containing an anti-CD14 antibody molecule-expressing nucleic acid thereof.

5. The method of claim 3, wherein the monoclonal antibody is comprised of an Fab, Fab', F(ab')$_2$, or F(v) portion of the anti-CD14 antibody molecules.

6. The method of claim 3, wherein said therapeutically effective amount is 0.2 to 20 milligrams per kilogram body weight per day.

* * * * *

UNITED STATES PATENT AND TRADEMARK OFFICE
CERTIFICATE OF CORRECTION

PATENT NO.    : 6,495,332 B2
DATED         : December 17, 2002
INVENTOR(S)   : Ulevitch et al.

It is certified that error appears in the above-identified patent and that said Letters Patent is hereby corrected as shown below:

<u>Column 1,</u>
Line 19, prior to the "DESCRIPTION" section, please insert the following:
-- GOVERNMENTAL SUPPORT
This invention was made with government support under Contract Nos. NIH AI 15136, GM 37696, AI 25563, AI 22003 and AI 24775, and by the National Institutes of Health. The government has certain rights in the invention. --

Signed and Sealed this

Tenth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,495,332 B2
DATED : December 17, 2002
INVENTOR(S) : Ulevitch et al.

It is certified that error appears in the above-identified patent and that said Letters Patent is hereby corrected as shown below:

<u>Title page,</u>
Item [73], Assignee, please replace "The Sripps Research Institute" with -- The Scripps Research Institute --.

Signed and Sealed this

Seventh Day of September, 2004

JON W. DUDAS
*Director of the United States Patent and Trademark Office*